United States Patent [19]

Nakayama et al.

[11] Patent Number: 5,111,410
[45] Date of Patent: May 5, 1992

[54] MOTION ANALYZING/ADVISING SYSTEM

[75] Inventors: Mizuo Nakayama; Shigesumi Kuwajima, both of Tokyo; Takahito Suzuki, Kanagawa; Kazushi Miyake, Tokyo; Tsutomu Shibata; Chikashi Seki, both of Kanagawa, all of Japan

[73] Assignee: Kabushiki Kaisha Oh-Yoh Keisoku Kenkyusho, Tokyo, Japan

[21] Appl. No.: 543,127

[22] Filed: Jun. 25, 1990

[30] Foreign Application Priority Data

Jun. 23, 1989 [JP] Japan ................... 1-161299
Mar. 22, 1990 [JP] Japan ................... 2-72841
Apr. 13, 1990 [JP] Japan ................... 2-98485

[51] Int. Cl.⁵ ................... A61B 5/11; A63B 69/36
[52] U.S. Cl. ................... 364/551.01; 273/183 R; 358/105
[58] Field of Search ................... 364/551.01, 550, 559, 364/577, 413.01, 413.13, 518, 521, 410; 358/105, 107; 273/35 R, 183 R, 32 R; 340/323 R; 354/410, 412; 434/252, 258, 307

[56] References Cited

U.S. PATENT DOCUMENTS

| | | | |
|---|---|---|---|
| 3,820,130 | 6/1974 | Cornelison, Jr. et al. | 354/76 |
| 4,163,941 | 8/1979 | Linn, Jr. | 324/178 |
| 4,631,676 | 12/1986 | Pugh | 364/413.01 |
| 4,713,686 | 12/1987 | Ozaki et al. | 354/416 |
| 4,891,748 | 1/1990 | Mann | 273/183 R |
| 4,896,283 | 1/1990 | Hunt et al. | 364/577 |
| 4,951,079 | 8/1990 | Hoshino et al. | 354/412 |
| 5,034,811 | 7/1991 | Palm | 358/105 |

Primary Examiner—Gary Chin
Assistant Examiner—Michael Zanelli
Attorney, Agent, or Firm—Cushman, Darby & Cushman

[57] ABSTRACT

This invention relates to a motion diagnosis system which picks up motions of a subject and analyzes them, and is characterized by measuring address data at points of images thus picked up according to a trigger condition set in advance, displaying the result of the measurement in graphic images or stored images or in comparison with reference images, outputting the evaluation of such comparison to thereby enable measurement under flexible trigger conditions and analyzing the motions of the subject based on quantitative data in a manner easily understandable by the viewers and simple operation.

23 Claims, 24 Drawing Sheets

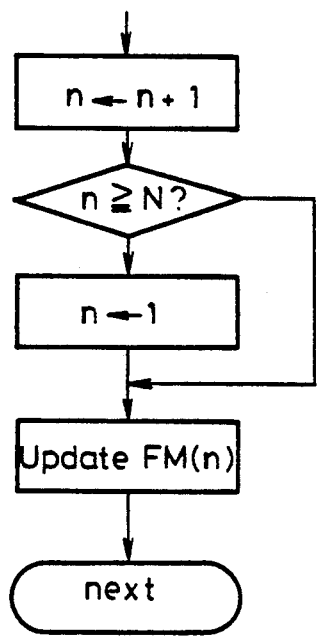
FIG. 25
FIG. 26
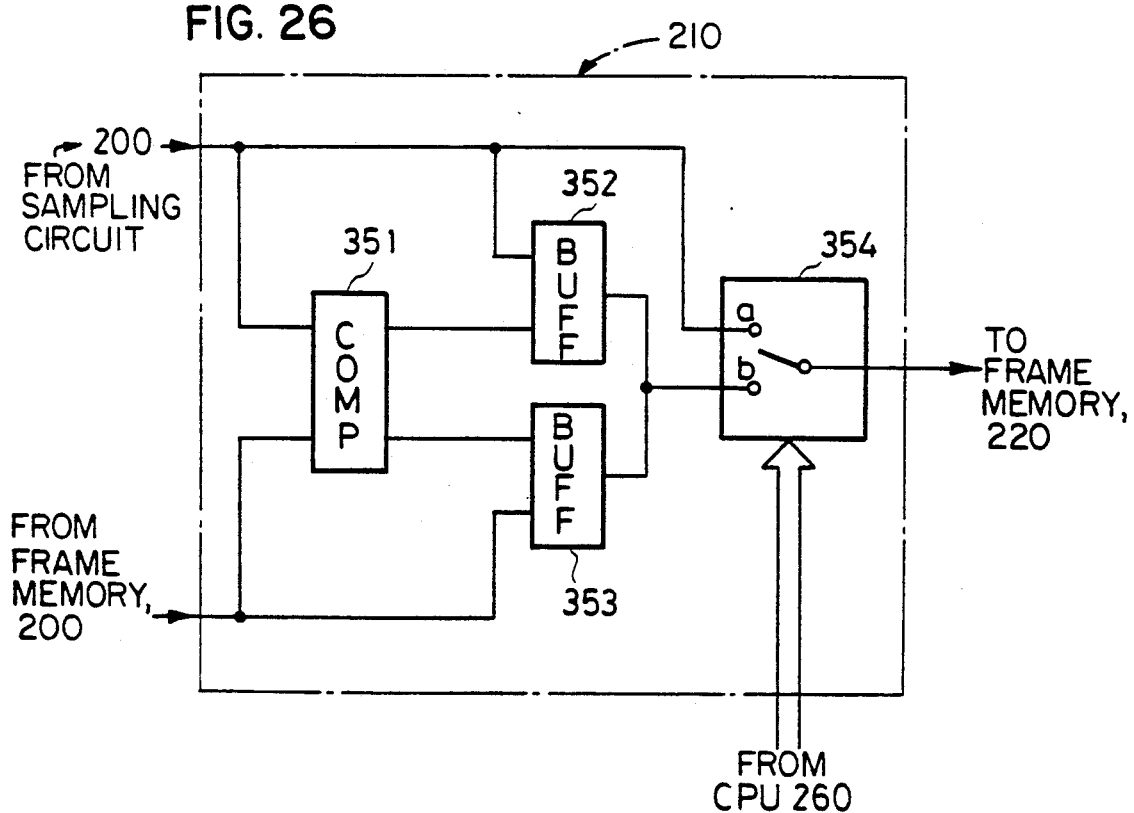

MOTION ANALYZING/ADVISING SYSTEM

This invention relates to a system which measures, analyzes and diagnoses motions of humans. This invention relates, more particularly, to a system which displays in images the result of analysis of photographed golf swings and of comparison thereof with reference data, synthesizes images of swings with extracted data, displays stick patterns thereof for the reference of learners and/or obtains the difference between their motion and the target motion to diagnose their skills.

This invention further relates to the technology used in a system which generates signals for start, suspension or end of measuring, recording and displaying when the system measures motions for analysis. This invention is applicable to a system for analyzing/teaching golf swings.

BACKGROUND

Analysis/evaluation of motions of a player of sport has usually been performed by an instructor. For instance, when a golf player practices swings, an instructor watches the player's motion and gives appropriate advices. If such an instructor is not available, the player records his swings in VTR or films and shows them later to the instructor for advise.

There has been proposed a memory means which can pick up swing forms of a player in VTR or in time lapse shooting; for example, a technology which picks up swing forms of a player by an electronic-still-camera and reproduces/displays them in the unit of frames to viewers.

There has also been proposed in the prior art a system for evaluating golf swings which measures the speed or direction of a golf ball or the impact speed of a club head and digitally displays the result in numerical figures.

Although there is also available a system which picks up swings in image and processes them, there has heretofore been no system which can analyze the captured swings in real time, compare them with a reference, and give suitable advises. When a golf player wishes to practice by himself without an instructor, he cannot achieve an effective result because he is without valuable advises. Unless he is given timely advises while he still remembers his motion, his practice cannot attain effective result. If he is given instruction after a time lapse, learning effect cannot be fully achieved.

Even if a player is shown his swings in image which are reproduced in the unit of a frame, an amateur player merely sees his motions which he cannot evaluate properly and hence cannot benefit from the display. Data in numerics are not useful in evaluating his motions, since such display of numerical values alone does not show his whole actions nor diagnose his swings. All these conventional systems are therefore defective as a teaching system for golf swings.

Moreover, these prior art systems measure motions of a player by means of switches. More particularly, measurement is taken for 3 seconds after a switch is turned on; this takes unnecessary measurements before and after a motion. In order to eliminate such waste, the system requires manual operation by an assistant other than the player himself for turning on the switch. The conventional system, moreover, cannot precisely catch motions if they are very quick.

There has also been proposed a method of starting measurements by means of a sensor such as an optical limit switch. For instance, there has been proposed a method which employees a lamp and an optical limit switch and which uses signals generated when a golf club crosses the path as trigger signals for measurement. But this method is defective in that an optical limit switch should be provided at a designated location, and that the position of such switch should be changed depending on the type of motions to be measured such as the motion of impact and the motion of follow-through. The system therefore is not adaptive to the subject of measurement or the degree or type of motions. It is also difficult to use the system with an optical limit switch to measure complicated movements.

As stated above, the conventional systems require additional manual operations or special sensors, and the trigger method thereof is not flexible enough. They cannot effectively detect some types of motions.

This invention aims to obviate these problems encountered in the prior art and to provide a motion analyzing/advising system which measures, analyzes, and evaluates motions in real time and outputs the result in display to diagnose them without the special sensors, etc. for triggering the system, and which can efficiently and effectively start the measurement operation from the image information of the motions.

SUMMARY OF THE INVENTION

The first aspect of this invention provides a motion analyzing/advising system which can pick up motions of a golf player and displays the data of his movements at critical points in images with reference data.

More particularly, this invention provides a motion analyzing/advising system including a means which samples images of motions of a subject player and converts them to digital signals, a measurement means which extracts positional data from digitized image data for a plurality of motion points which are preset for motion analysis, and a display means which displays the result of measurement by the means, which is characterized in that the system further comprises a means which displays simultaneously the positional data at the motion points extracted by the measurement means together with the positional data of reference.

It is desirable to display positional changes in the address coordinates against time at one point with the chronological changes of the reference point. It is also desirable to display the track of a motion of at least one point together with the track of the reference point.

The second aspect of this invention provides a motion analyzing/advising system which displays the movements of motion points in address superposed on the images of the motions of the subject player. More specifically, the system is characterized in that an image memory means for storing picked up images is provided so that positional data of at least one point may be displayed in the display means overlappingly with the images stored by the memory means. It is desirable to display the track of at least one motion point simultaneously with the images stored in the image memory means at preset timings.

The third aspect of this invention provides a motion analyzing/advising system which picks up motions of a subject player and displays them in stick pictures by connecting points of his motions with line. The system is characterized in that it further comprises a means which connects motion points with lines, and a means which displays linear components between these connected motion points for plural frames. The system preferably includes a means which calculates by arithmetic operation the positional data of a point designated in advance out of the address data of surrounding points, and a means which displays in emphasis the line between the motion points at a time point designated based on the calculated value. It is also desirable to display the line between motion points together with the images stored in the image memory means.

The fourth aspect of the invention provides a motion analyzing/advising system which picks up motions of a subject player, extracts data representing features of the motion, compares the data with the reference data and outputs the result of diagnosis based on the difference between the reference and the analysis subject.

The motion analyzing/advising system according to this invention includes a sampling means for sampling images of motions of a player and converts them into digital signals and a measuring means for extracting positions in coordinates for each point of plural motions which are preset for analyzing the motions, and is characterized in that the system further comprises a data calculating means for calculating data representing features of the motion out of the coordinates of each point extracted by said measuring means, a comparing means for comparing the thus calculated data obtained by the data calculating means with the reference data to obtain an evaluation value, and an output means for selecting one of the diagnoses prepared in advance depending on the thus obtained evaluation value.

This invention system includes plural references and can compare the data of a subject player with those plural references. The system may further include a means which judges to which reference the player's data is closest. It may include a means to select plural references, and the comparing means can compare the data of the player with the thus selected plural references.

The data calculating means desirably includes a means which can convert data of two or more points which have been already calculated into the data of the same time point as the reference data.

The measuring means preferably includes a tracking means which designates areas including one or more motion points, moves the areas in the directions of the motion points respectively, and outputs the positional coordinates of the points.

It is preferable to output the result of the diagnosis in voice, and the motion to be diagnosed may be a swing in golf playing.

The fifth aspect of this invention provides a motion analyzing/advising system which can automatically execute the start, suspension and completion of operations without the necessity of providing an additional sensor. More particularly, the motion analyzing/advising system according to this invention includes a sampling means for converting images of the motions of a player into digital signals, a calculating means for calculating positional data in address for a plurality of motion points out of the thus converted image signals, and a measuring means for starting, suspending or finishing a measuring operation based on said positional data, and is characterized in that the system further includes a trigger detection means for detecting whether said motion points meet trigger conditions which are predetermined for starting, suspending or finishing the operation based on said address data.

The trigger detection means preferably includes a means for detecting whether a motion point forms a predetermined angle in the reference direction, or whether the motion point forms a predetermined angle in the reference direction at a speed higher than the predetermined speed.

The trigger detection means preferably includes a means for detecting if a motion point has passed a preset area in the address at a speed higher than the predetermined speed. The system may include an image memory means for storing images which are picked up with a trigger signal outputted from the trigger detection means in a plurality of frame memories, and the image memory means preferably includes a means which can overwrite images stored in a frame memory over the picked up images in superposition.

Preferably, the system includes one or more memories for storing the results of measurement and a means for prohibiting writing in the memory with a trigger signal outputted from the trigger detection means.

The system preferably includes an instruction means for instructing reversing if a mirror image is to be picked up or if a subject player is left-handed, a means for reversing an image, a means for reversing the positional data in the coordinates of motion points, or a means for reversing the trigger conditions or rotation.

The motion analyzing/advising system of the first to the fifth aspects of the present invention may be packaged in a transportable case and may be provided with a battery for driving the means thereof.

According to the first to the third aspects of this invention, the system takes in motions of a subject player including his swings as image data, measures them, displays the measured data with images at any particular desired time point or displays stick pictures of his swings. According to the fourth aspect of this invention, the system can render diagnoses on various and different aspects depending on the reference, and therefore dispenses most suitable advice for each target model. As the system judges to which pattern the motion of a player belongs, and gives advices suitable to the particular pattern, it can teach any player in a most appropriate and effective manner depending on his motion type. Motions of a player including swings can be objectively evaluated irrespective of his build.

According to the fifth aspect of this invention, the system can execute measurement adaptive to the content of the subject motions, and therefore can provide flexible and most effective measurement adaptive to the content of the subject without waste.

The system according to the first to the fifth aspects of this invention is compact in size and simple in use. The system is therefore highly effective if installed at golf driving ranges or used for self-teaching.

BRIEF DESCRIPTION OF THE DRAWINGS

The invention will be better understood by reference to the drawings, in which:

FIG. 25 is a flow chart showing the operation of processing A in FIG. 24;

FIG. 26 is a chart showing the construction of an image switching calculating circuit;

DESCRIPTION OF THE BEST MODES FOR EMBODYING THE INVENTION

This invention is now described referring to an analysis of golf players' swings, but this invention is not limited to golf swings but may be applicable to analysis and instruction for baseball batting, gymnastics forms, etc.

Figure 1:
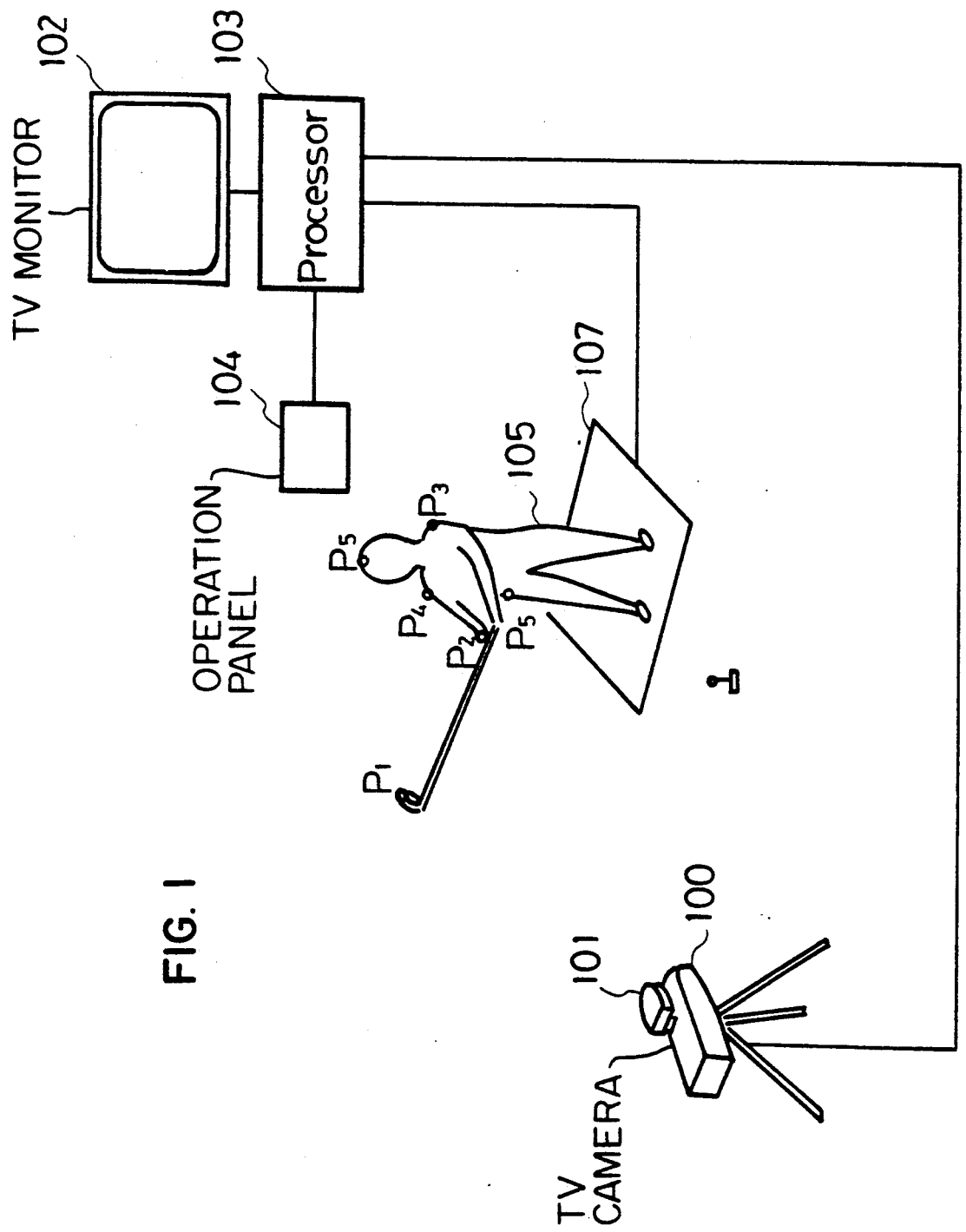
FIG. 1 shows a golf swing analyzing/advising system embodying this invention.

FIG. 1 shows the structure of an embodiment of a golf swing analyzing/advising system according to this invention. The system comprises a TV camera 100 which picks up the swings of a subject player 1051, a lighting unit 101 appended to the TV camera 100, a processor 103 which inputs images taken by the camera 100 and processes data for image processing, measurement, diagnosis and display, a display for monitoring 102 which displays images, and an operation panel 104 provided with various switches for setting display modes or diagnostic conditions and lamps to indicate an operation mode. The body of the player 105 and a golf head are pasted with retro-reflective tapes to designate motion points $P_1$ (a golf club head), $P_2$ (the player's wrist), $P_3$ (his right shoulder), $P_4$ (his left head), $P_5$ (his head), and $P_6$ (his hip). The intensity of light reflected from the points $P_1$ through $P_5$ is detected and measured to extract the positional data in an address for each point.

The system further includes a force plate 107 on which the player 105 stands when he starts his swings, and outputs therefrom are inputted at the processor 103. The force plate 107 measures displacements of both the weight of the player and distribution of his weight between his feet, and further the fluctuation of these values supplementally to further enhance the effect of this system in evaluation and analysis of his motion.

Figure 2:
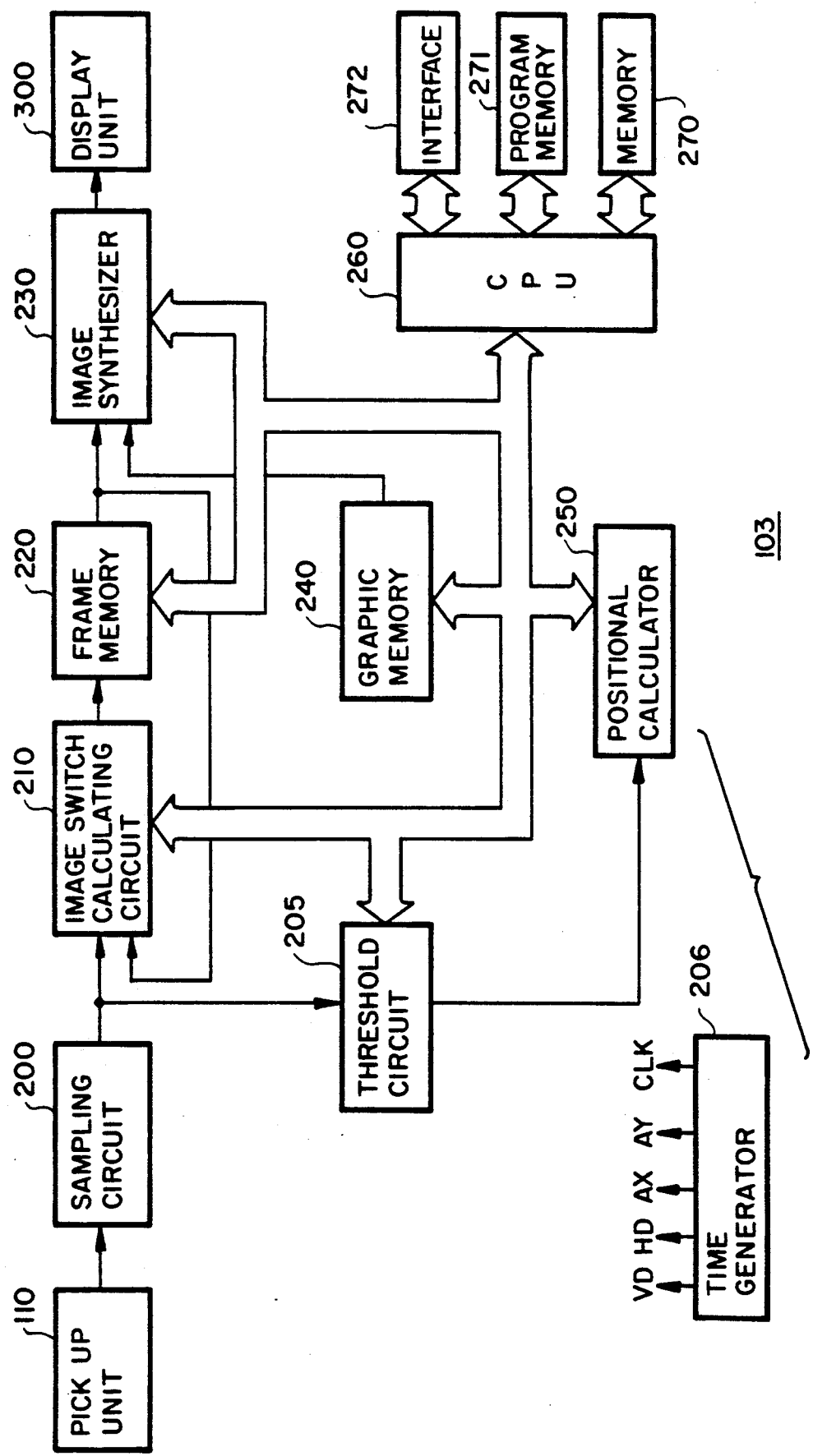
FIG. 2 is a block diagram of an embodiment of a processing system.

FIG. 2 is a block diagram to show the structure of the processor 103 which comprises a sampling circuit 200 which samples video signals inputted from a pick up unit 10 including a TV camera 100 and a light source 101 according to clock signals CLK from timing generator 206 and converts them into digital signals. Threshold circuit 205 binarizes the output image signals from the sampling circuit 200, and a coordinate calculating circuit 250 calculates the position of a point P in accordance with the output from the threshold circuit 205. Address calculating circuit 250 calculates the position in the coordinates of the point P based on the output from the threshold circuit 205. Frame memory 220 stores image signals outputted from the sampling circuit 200 in the unit of a frame and has a capacity to store images of plural frames, while an image switching calculating circuit 210 controls initialization, renewal and saving of the frame memory 220 and selects images which should be stored therein. A graphic memory 240 stores character/graphic data for linear display or the measurement result or the output or operation thereof. A CPU 260 feeds timing signals to be stored in the frame memory 220, calculates the tracks of motion points out of the address data of the points, judges whether the preset trigger conditions are met, compares the data with a reference, and executes other various data processing and controlling operations. Memory 270 saves the measured values and stores the positional data for the points $P_1$ through $P_6$ or the data calculated therefrom, and program memory 271 stores the processing procedures for the processor. An interface 272 connects various peripheral parts such as an operation panel 104, an image synthesizer 230 which synthesizes the output images from the frame memory 220 or from the graphic memory 240 or both under the control of the CPU 260 and outputs the composed images to a display 300. Timing generator 206 generates not only clock signals CLK for timing, but also horizontal synchronizing signals HD, vertical synchronizing signals VD, and address signals AX and AY of the images and feeds them to necessary circuits. The display 300 shown in FIG. 2 is identical to the one for monitoring 102 shown in FIG. 1.

The frame memory 220 is an image memory which can independently control the input/output image signals in parallel, and which can record/reproduce TV video images in pieces (or 3 frames). The frame memory 220 is switched by controlling CPU 260. In order to save input images at a certain time point without updating the content of the frame memory 220, CPU 260 must control the system to invalidate writing-in signals on the input side thereof. This permits storage of images of an arbitrary frame and reproduction thereof on the display 300.

Figure 3:
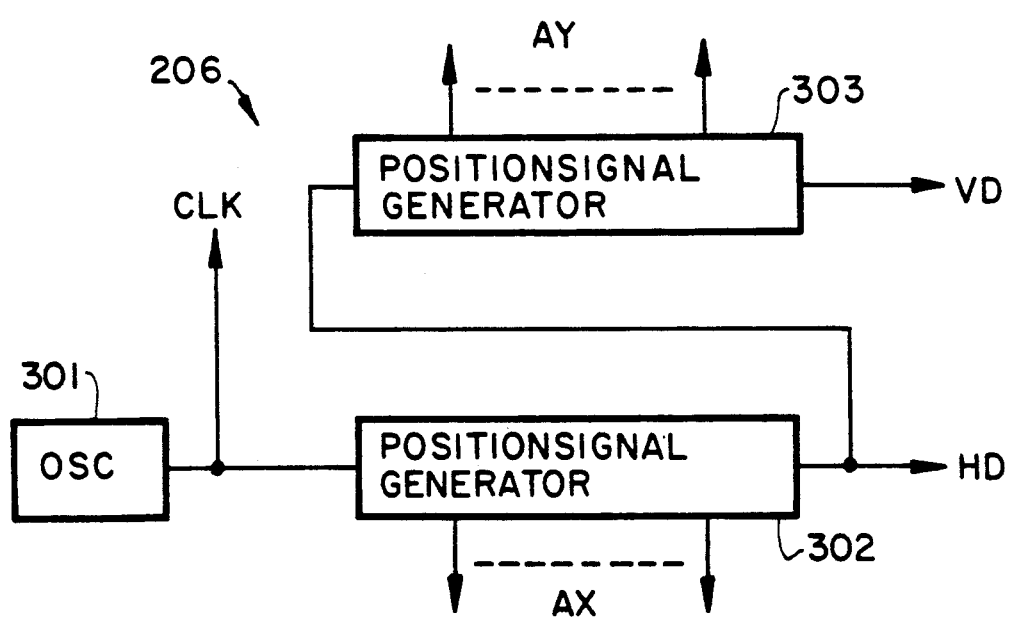
FIG. 3 shows an embodiment of a timing signal generator useful in FIG. 2.

FIG. 3 shows the structure of a timing generator 206 which generates timing signals by dividing in frequency the clock signals generated by a crystal oscillator to generate horizontal synchronizing signals HD and vertical synchronizing signals VD of images, and counting these horizontal and vertical synchronizing signals to generate address signals AX and AY and supplies them to necessary circuits. More particularly, the clock signals CLK outputted from the oscillator 301 are applied to a position signal generator 302 which generates respective X-coordinate signals AX, and the outputs from the circuit 302 at the opposite terminal are outputted as horizontal synchronizing signals HD. The horizontal synchronizing signals HD are applied to another position signal generator 303 which generates respective Y-coordinate signals AY. The outputs from the circuit 303 from the opposite terminal are outputted as vertical synchronizing signals VD. The generators 302 and 303 comprise shift registers.

When the clock signals CLK are set at 6.13 MHz, the horizontal synchronizing signals HD at 15.72 KHz, and the vertical synchronizing signals VD at 60 Hz in practice, a screen as a whole may form a coordinate system having 320 coordinates in the X (horizontal) direction and 240 in the Y (vertical) direction.

It is assumed that the center of the address coordinates of a screen is set at (0, 0), the right upper end at (159, 119), and the right lower end at ($-160$, $-120$). The trigger conditions which will be described hereinafter may be designated in the address after conversion or may be designated in the actually measured length and converted later into the address values.

Figure 4:
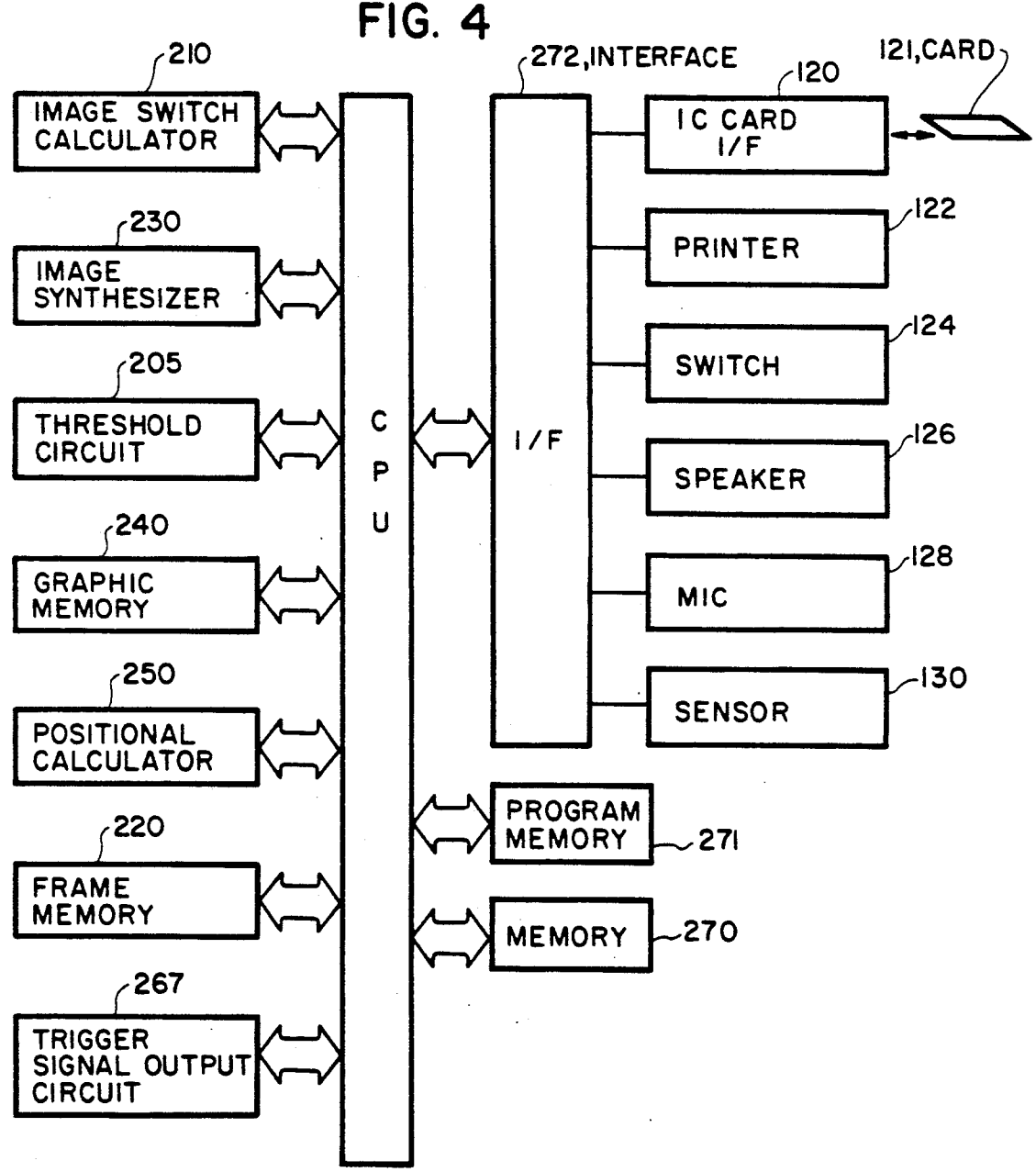
FIG. 4 shows the peripheral components of the CPU's of FIG. 2.

FIG. 4, which is similar as to its elements to FIG. 2, differently shows the peripheral equipment associated with the CPU 260 which is connected by buses respectively to the threshold circuit 205, a graphic memory 240, a positional calculator 250, an image switch calculator 210, a frame memory 220, an image synthesizer 230, a trigger signal output circuit 267, a memory 270 to save measured values, etc., a program memory 271, and an interface 272 which interfaces with various peripheral devices. To the interface 272 are connected a switch 124 of the operation panel 104, a data input/output device 120 for IC card 121, a printer 122, a speaker 126, a microphone 128 and a sensor 130. CPU 260 is connected to a window signal generator and to voice synthesizers, whenever necessary.

Figure 5:
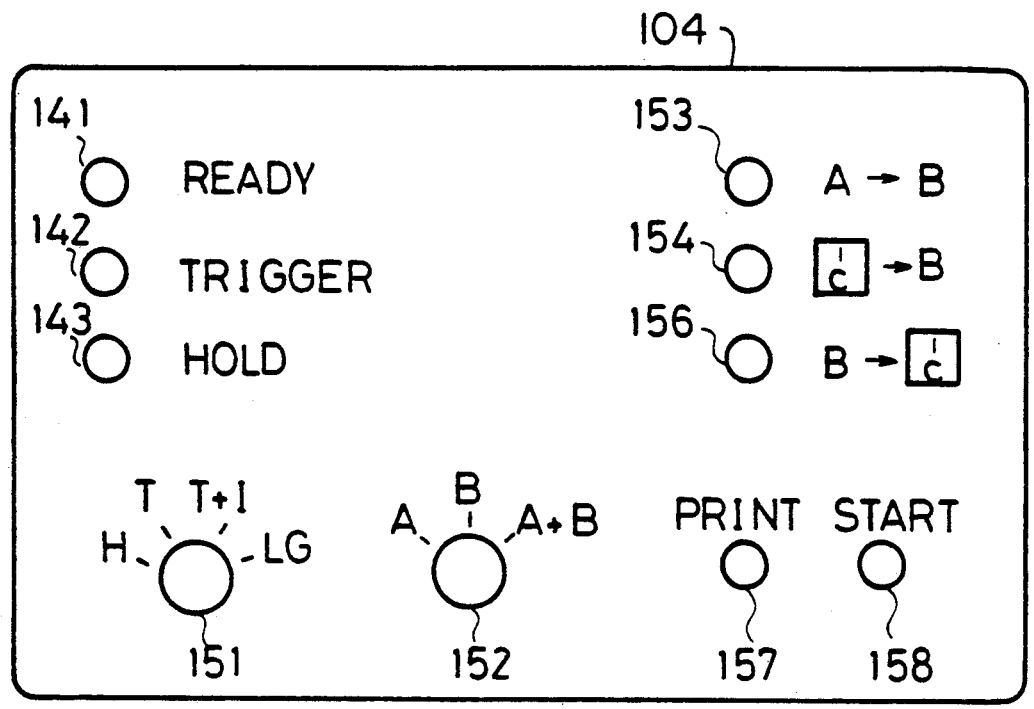
FIG. 5 shows an embodiment of the operation panel of FIG. 1.

FIG. 5 shows an operation panel 104 according to the first through the fourth aspects of this invention. The panel is provided with lamps 141, 142, and 143 which indicate at which mode the operation is currently being conducted; i.e. "ready", "trigger" or "hold" at the left upper side of the panel. The panel is also provided with a switch 151 which shifts the panel between the mode to output the changes in motion points in graphs, tracks or composite images of tracks with images stored in the frame memory 220 or the mode to display them in linear images obtained by connecting the motion points with lines. Switch 152 instructs shifting between the swing images A which is the subject of the analysis and the model images B. Switch 153 instructs writing of the data within the saving area A of the result of the measurement into the saving area B for comparison purpose. Switch 154 instructs reading in of the image data of the reference swing stored in the IC card 121. Switch 157 instructs the print out of the result of the measurement, and switch 158 operates to start the shooting.

Figure 6:
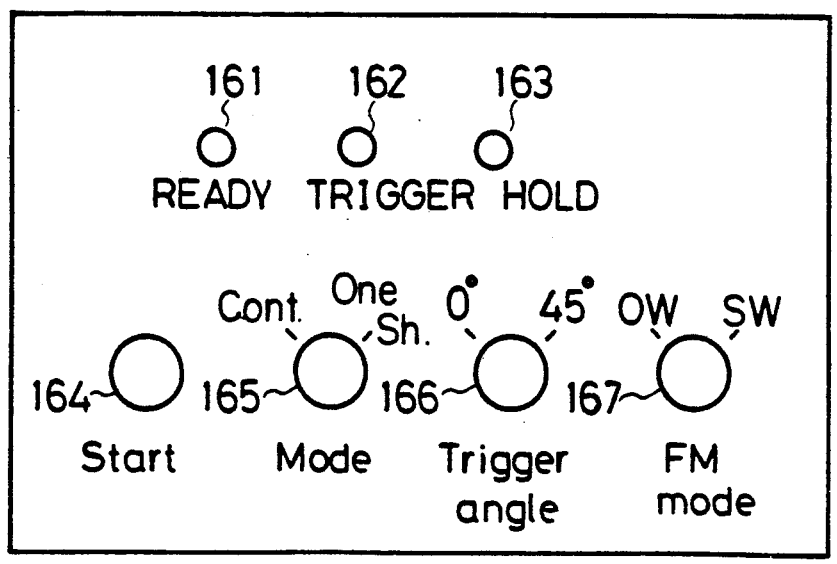
FIG. 6 shows another embodiment of such an operation panel.

Another embodiment of the operation panel is shown in FIG. 6. The panel is structured for trigger designation indicated in the fifth aspect of this invention.

At the upper end of the panel, there are provided lamps 161, 162, 163 to indicate the mode of "ready", "trigger" or "hold". Switch 164 starts the shooting for measurement of a swing, a mode switch 165 to indicate whether the measurement is continuous or one-shot shooting. Switch 166 designates trigger timings by angles for storing in the frame memory 220, and switch 167 indicates whether the mode of the frame memory 220 is "overwriting" or "single writing".

Before describing the operation of an embodiment of the system, explanation is given to the structure which calculates motion points P in the coordinate calculating circuit 250 where window signals are used to generate window areas set around the motion point P.

Figure 7:
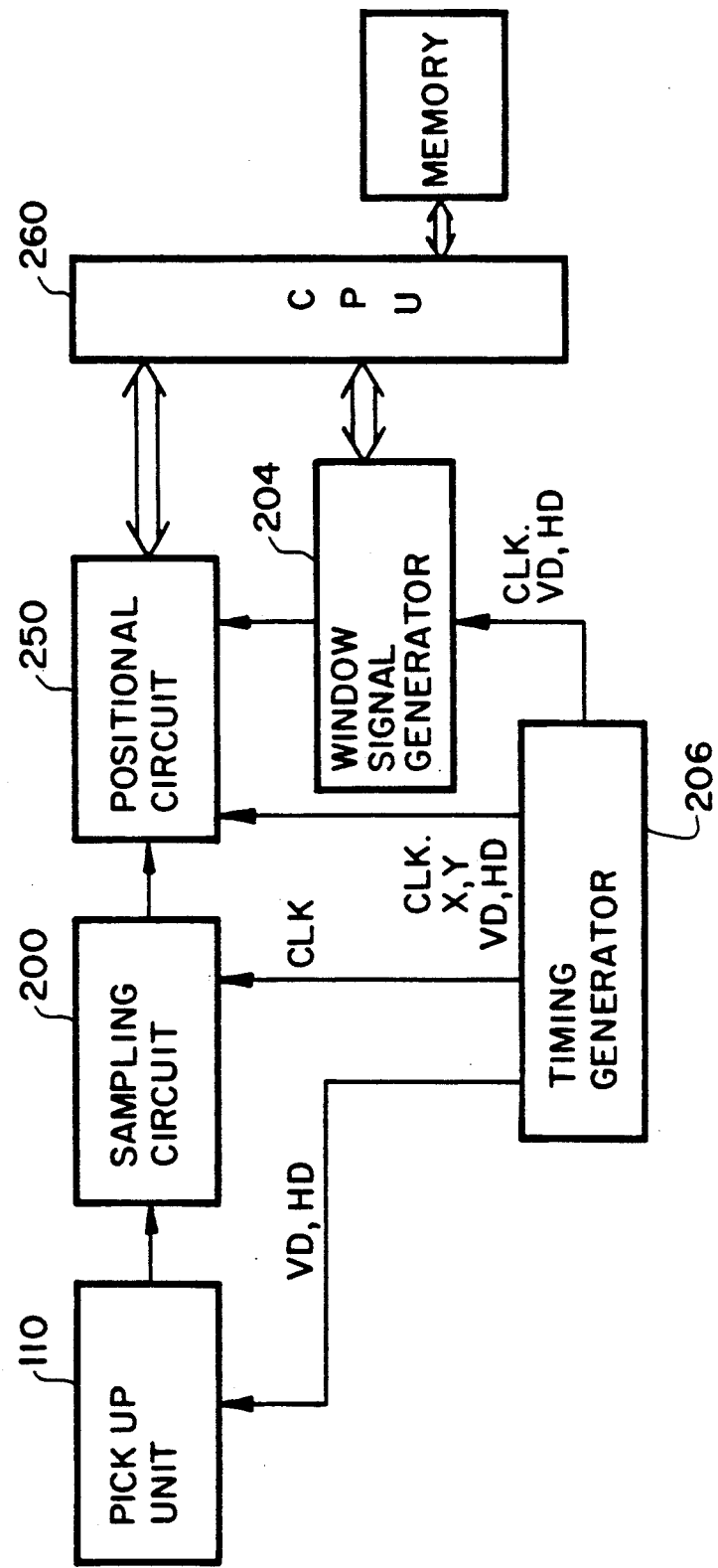
FIG. 7 shows an arrangement for calculating motion points positional data.

FIG. 7 shows connections to the positional or coordinate calculating circuit 250. More particularly, the circuit 250 receives as input the window signals generated from the window signal generator 204 and uses the signals to calculate addresses of the motion points $P_1$ through $P_6$. Although the threshold circuit 205 is omitted and signals are directly inputted from the sampling circuit 200 in this figure, the signals are inputted to the calculating circuit 250 via the circuit 205 as shown in FIG. 2. Alternatively, the system may be so structured that signals are calculated in the form of color signals without being converted into binary signals by the circuit 250.

FIG. B shows the structure of the window signal generator 204. The circuit 204 accurately tracks the movements of plural points P to detect their positions in the coordinates even if the plural motion points are moving separately. The circuit 204 may delete processing for addresses of the points other than the necessary ones for analysis to thereby reduce the amount of processing by the circuit 250 and CPU 260.

The circuit 204 is structured to output the window signals WS by multiplication of the signals in the direction X with the signals in the direction Y. The circuit in the direction X includes a counter 341 which inputs horizontal synchronizing signals HD and clock signals. Comparators (COMP) 342, 343 compare the output of X signals from the counter 341 with $X_1$, $X_2$ signals which set the frame addresses in the direction of X for the window signals fed from CPU 260. AND circuit 344 outputs window signals in the direction X when X direction signals outputted from the counter 341 based on the multiplication with the outputs from the comparators 342 and 343 satisfying the condition $X_1 \leq X \leq X_2$. Similarly, circuit 204 includes in the Y direction, a counter 345 which inputs the vertical synchronizing signals VD and clock signals CLK. Comparators 346, 347 compare the Y direction signals with $Y_1$ and $Y_2$ signals fed from CPU 260. AND circuit 348 receives the output from the comparators 346 and 347. The AND circuit 349 receives the outputs from the AND circuits 344 and 348 to output the window signals WS to the circuit 250.

Figures 8, 9:
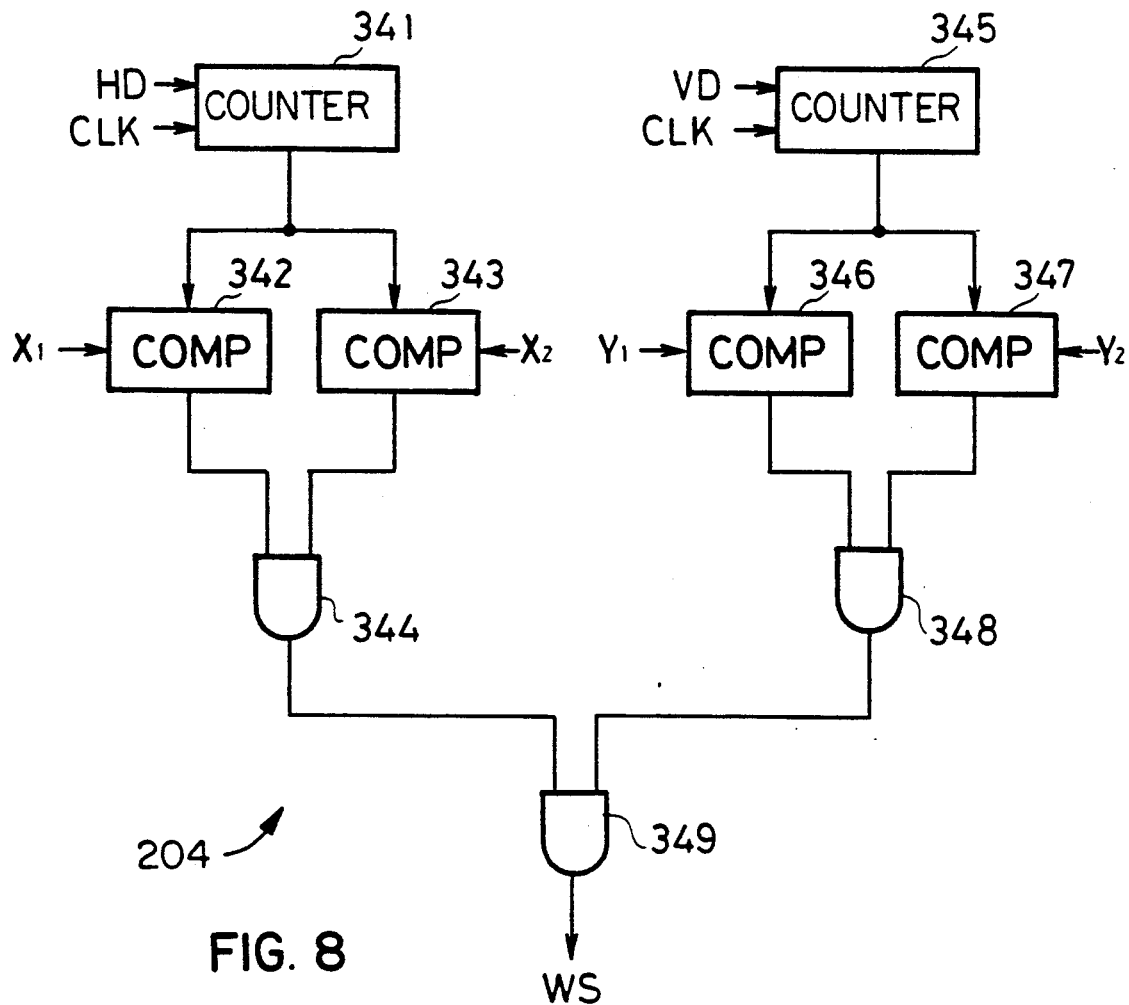
FIG. 8 shows a window signal generator.
FIG. 9 shows an embodiment of a window.

FIG. 9 shows an example of a window formed with such window signals. An area surrounding the point P and circumscribed by the conditions $X_1 \leq X \leq X_2$, $Y_1 \leq Y \leq Y_2$, is defined as a window and addresses of the point P within the frame are outputted from the circuit 250. The area of the window moves along the movement of the point P in the same direction. The window area is moved sequentially in the direction of the movement of the point P obtained by CPU 260.

The example shown in FIG. 9 is the case where only one window is formed, but in practice addresses are calculated for plural motion points $P_1$ through $P_6$, and hence the FIG. 8 window signal generator 204 would be in number equivalent to the number of motion points.

Operation of this system is now described. The explanation on the operation of this embodiment comprises three parts; (1) the first part concerns the first to the third aspects of this invention and, more particularly relates to the operations of picking up the golf swings and measuring them, displaying the movements of the motion points in graphs, tracks and linear displays as the result of the measurement in composition with the images stored in a frame memory; (2) the second part relates to the fourth aspect of this invention or the operation to compare the obtained data with the reference data stored in advance in the system to obtain the distance from the reference, and to output the result of various diagnoses in voice according to the distance; and (3) the third part relates to the fifth aspect of this invention or the operation to trigger the measurement or the operation to collect data, to save images or suspend or complete measurement when predetermined conditions for trigger are met.

The description will be given first in respect of the operation related to the first through the third aspects of this invention. A swing motion of a golf player is assumed herein to be diagnosed by the following four displays. The first one is a graph display on a display 300 having the time on the horizontal axis and changes in height on the vertical axis in order to show the positional data of the picked up swinging form of the player and the difference from the reference model. The second is the display of the track of motion points in combination with the tracks of model forms. The third is the display of a motion point track of the player in combination of the image of the swing which is most approximal thereto at a certain given time, such as impact, of those stored in the frame memory 220. The fourth is the display on the display unit 300 of a linear pattern formed by connecting motion points with lines to show the swing of the player in stick patterns. For this operation, an image switch calculator 210 is not used.

These displays may be selected by a switch on the operation panel 104 (FIG. 5). By turning on the start switch 158, the system is actuated and the TV camera 100 (FIG. 11) of the unit 110 (FIG. 2) picks up the images of a swing of a subject player. Before shooting, retro-reflective tapes are pasted on the pertinent locations of the body of the player for analyzing his motion and these locations are denoted as the motion points $P_1$ through $P_6$. The attachment of retro-reflective tapes increases luminance on the points P, to P to facilitate extraction from the images. Extraction of the motion points P may be executed by colors. In such a case, a color TV camera and a color extraction circuit in the number equivalent to the maximum points of the output color image should be used.

As the player moves at high speed, it is preferable to use a strobe as the light source 10 for the TV camera 100 in order to capture the motion, and to flash the light in synchronization with video signals. A shutter camera may be used as the TV camera 100. In such a case, it may replace the strobe and is lit constantly as the light source.

The imaged swings of the player are converted into digital signals by the sampling circuit 200 (FIG. 2). Thus obtained image data in the form of digital signals are stored in the frame memory 220. The digital signals are binarized by the threshold circuit 205 and inputted at the circuit 250. The circuit 250 then converts the binary signals into x-coordinate signals and Y-coordinate signals, out of which positional signals related to the points $P_1$ through $P_6$ are taken in by the CPU 260 to calculate data for these points.

The image signals stored in the frame memory 220 are stored while plural sheets of the frame memory 220 are updated. The images at particular timings as instructed by CPU 260 such as the timing of impact are held.

The method of setting the timing for the frames which should be stored in the frame memory 220 or of setting trigger timings for calculation of positional signals for the points P is described hereinafter. A sensor may be provided so that the timing is set with the output from the sensor for saving or calculating the data in the frame memory 220.

Figure 10:
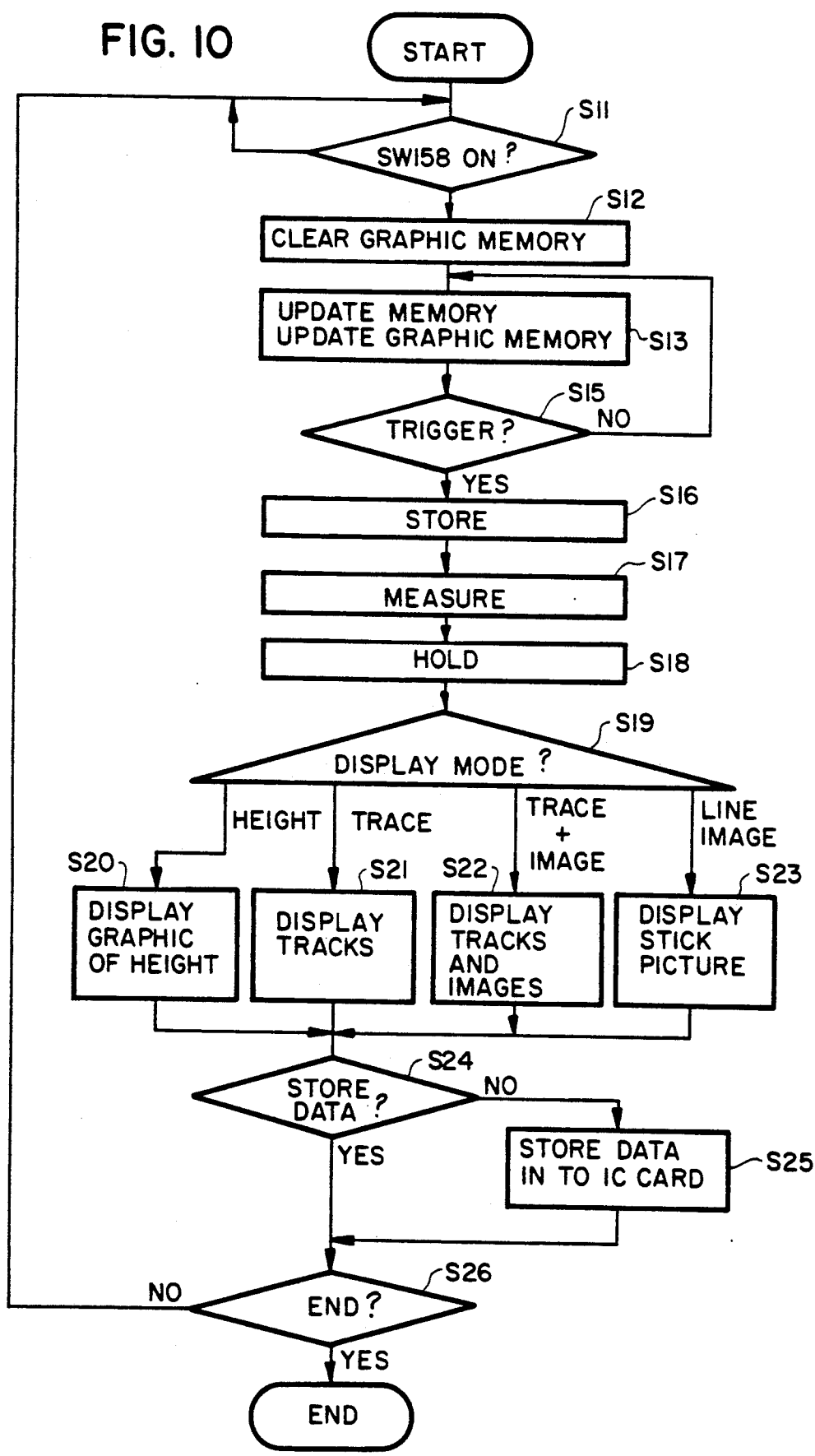
FIG. 10 is a flow chart showing the operation of an embodiment.

FIG. 10 is a flow chart to show the processing in the swing diagnosis by the processor 103. When the start switch is turned on, image signals are inputted and stored while the frame memories are updated, and the measured values are stored while the memory 270 is being updated and the graphic memory for display 240 is cleared (S11, 12, 13) at the same time.

When triggering starts, updating of the frame memory 220 is suspended and the images meeting the trigger conditions are held (S16). Measurement is continued for a predetermined duration of time after triggering, for instance for 0.5 sec., and the measured values are stored in the memory 270 to be held (S17, 18). This causes the measured values before and after triggering to be stored in the memory 270. If the trigger is set at the time of impact, therefore, positional data in motion points before and after the impact will be stored to enable formation and display of the tracks of the motions or in stick pictures.

Modes of display of the result of the diagnosis are selected from the graphic display of the changes in height of motion points (S20), display of the tracks of the points (S21), display of composed images of the tracks of the points and the swings stored in the frame memory 220 (S22), and display of the stick picture formed by connecting points with lines (S23). If data must be held, the data are stored in IC cards (S24, 25). Those four modes are respectively or sequentially displayed.

The operation will now be described more specifically taking example of the mode to display changes of height at the point $P_5$ or the head of the player. When a player swings, he should not move his head much, and therefore by displaying the changes in the height of his head, his performance may be evaluated.

The address data for the point $P_5$ inputted from the circuit 250 have been stored in the memory 270 as X- and Y-coordinate data. Out of the stored data, the changes in the height of the points of the values on the Y axis are extracted for the time from the start to the end of the swing, and are chronologically displayed in a graph. The graph is stored in the graphic memory 240. Simultaneously, changes in the height of the model swinging at the point $P_5$ are plotted chronologically in a graph and stored in the graphic memory 240.

Figure 11:
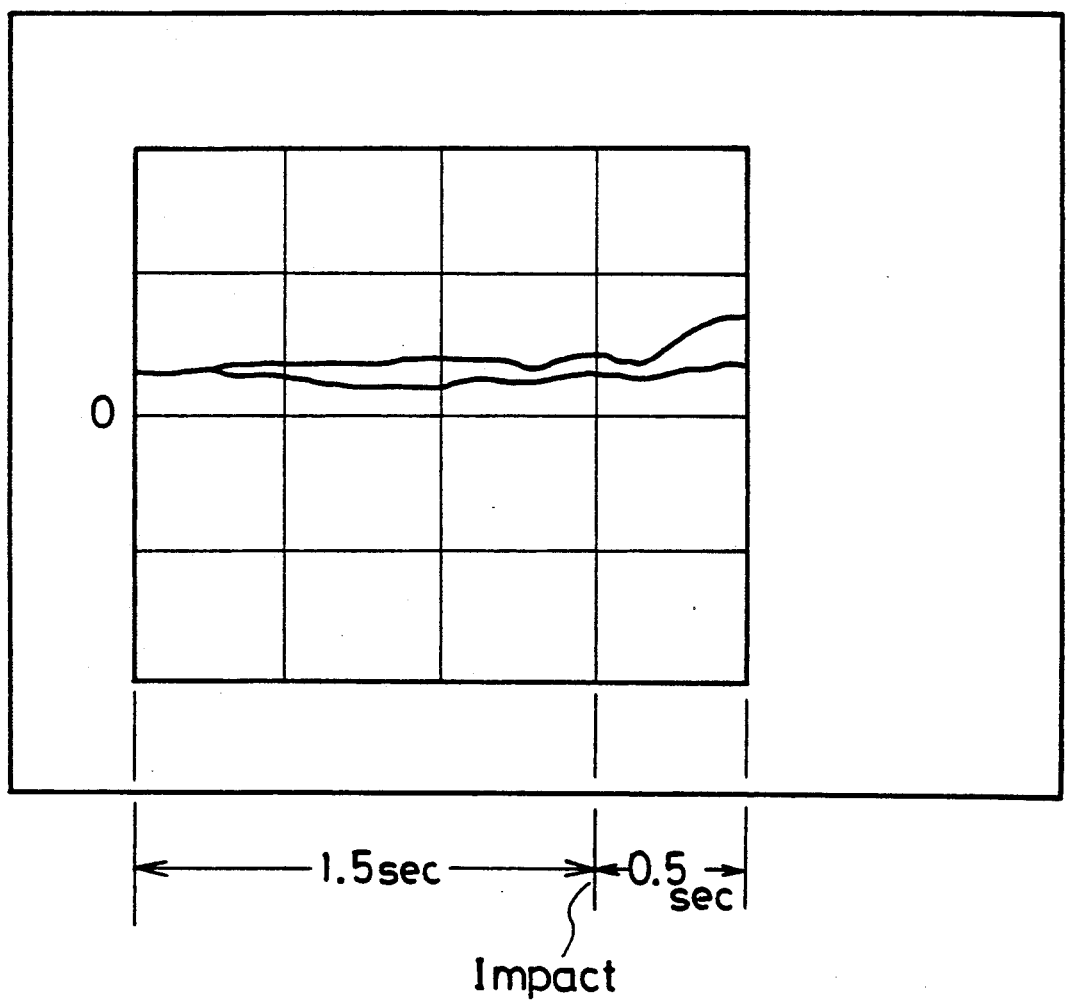
FIG. 11 is a graph illustrating the height indication.

By controlling the circuit 230, the output from the graphic memory 240 is displayed in the display unit 300. The two graphs are displayed in different colors so as to facilitate understanding of the viewer 105. An example of such display is shown in FIG. 11.

The displayed graph shows positional changes of the head of a player for 1.5 sec. before the impact and for 0.5 sec. after the impact. In the graph, the upper line indicates the positional change of the head of a skilled golf player while the lower line indicates that of a beginner. The graph clearly indicates that the beginner tends to move his head downward. Golfers can easily understand where their weak points lie by looking at the graph which indicates the reference model and their own movement.

The graph may be shifted horizontally so that the time of impact becomes the origin with deviation from the reference for better understanding by the viewer.

The operation to display the tracks of the points is now described. The positional data for the points P stored in the memory 270 are extracted, and the track thereof is stored in the graphic memory 240 based on the X- and Y-coordinates. Simultaneously, the data for reference points are stored in the memory 240 in the form of a locus. The two data are displayed in the display unit 300 via the circuit 230. The two loci should be displayed in different colors to facilitate understanding by the viewer.

Figure 12:
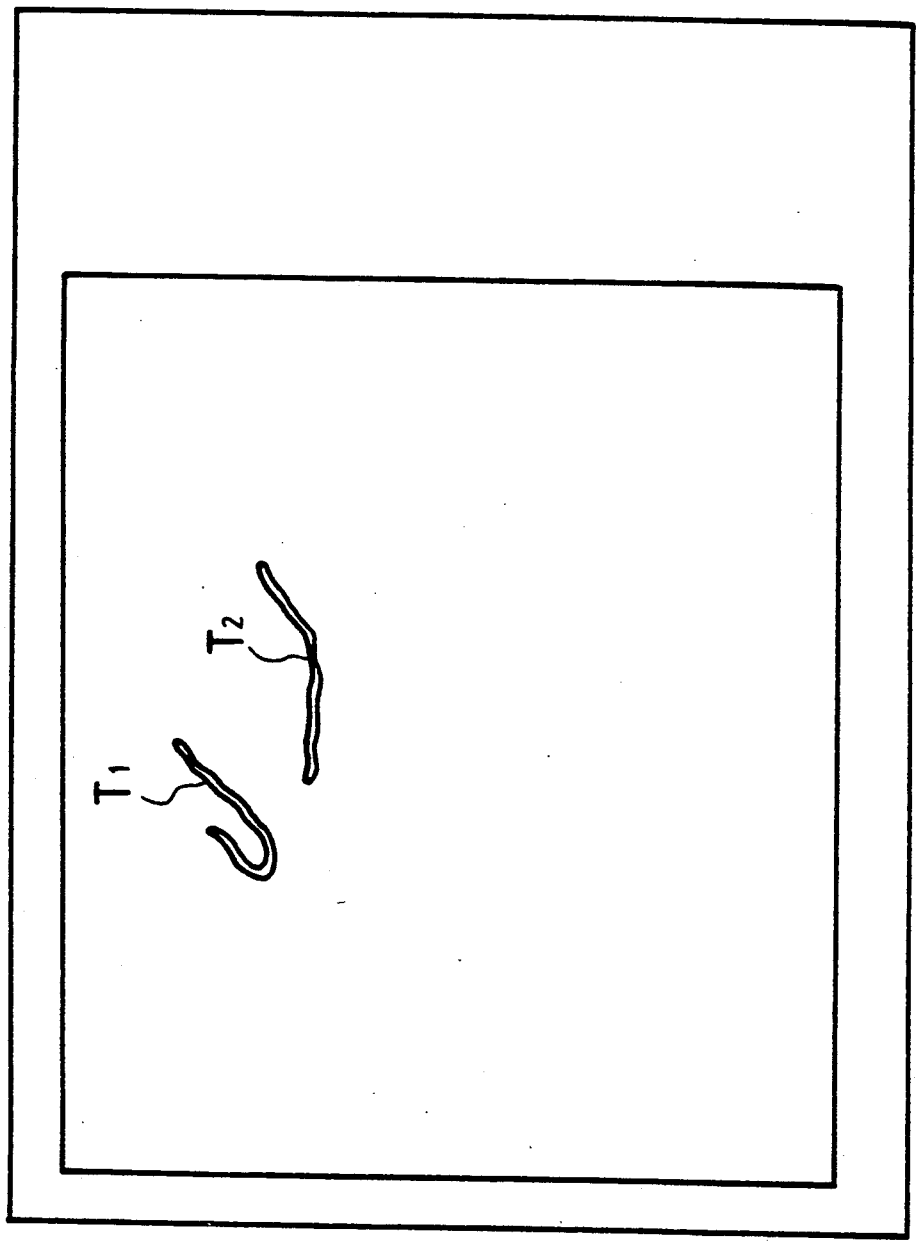
FIG. 12 shows an example of motion tracks.

An example of the display is shown in FIG. 12. The display shows in the form of loci the positional changes of the player's head at the point $P_5$. As the measurement is triggered at the impact, the time of the impact is displayed in a light color. In the graph, T1 denotes the locus of the movement of the player, and T2 the locus of the reference model. The graph may be plotted with the origin placed at the impact or the addressing time so as to show the data of the subject overlapping those of the reference model. If the locus before and after the trigger are plotted in different colors, understanding by the viewer is further facilitated. If the tracks of the point $P_2$ which is the wrist of the player, or of the point $P_1$ which is the position of his club head are plotted in the graph, it is preferable to plot them as a continuous locus by approximating them to a parabola because these points move radically.

The reference data may be the data of a professional golf player, the data of the subject player one month or one week before or the data taken when he practiced on his own. Such reference data is stored in the IC card 121 and the data may be inputted from the IC card input/output unit 120. Conversely, the measured data of his swing may be stored in the IC card 121 for use in the next analysis. IC card may be replaced by a floppy disc or the like.

The display of the composition of the images stored in the frame memory 220 and the locus of the movement is now explained.

The frame memory 220 stores image signals while updating the frames. The frame memory 220 stores and holds the frames which should be displayed later such as at triggered time when certain trigger conditions are met or the output from the sensor is received. The data on the tracks at the point P are also stored in the graphic memory 240.

If the display of the locus and of images are selected by the switch 151 on the panel 104, CPU 260 controls the system to display on the unit 300 the images of a swing stored in the frame memory 220 together with the locus stored in the graphic memory 240. The image synthesizer 230 is used to compose the two images and display the same on the unit 300.

Figure 13:
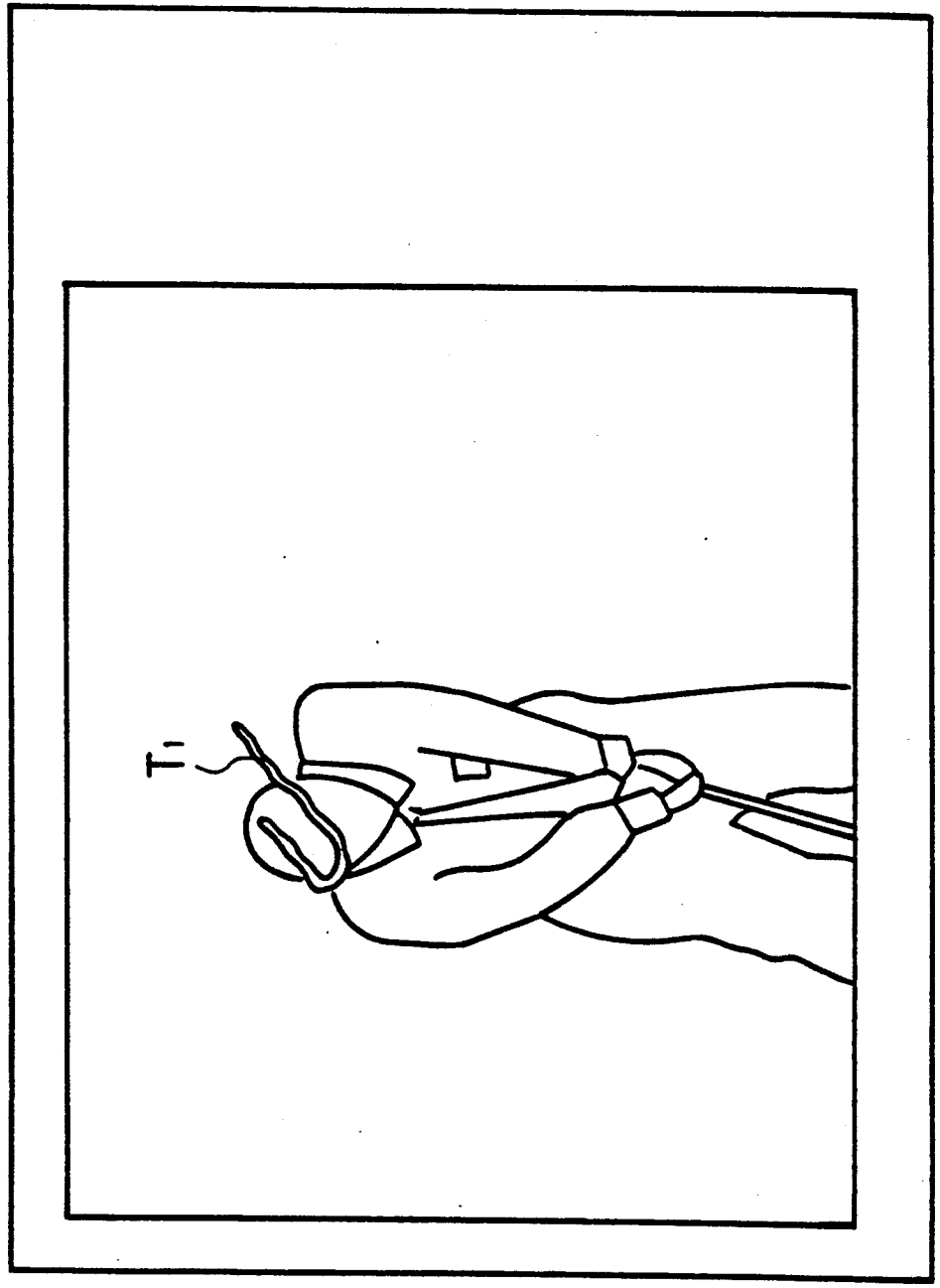
FIG. 13 shows an example of a synthesized display of a track and an image.

An example of the display is shown in FIG. 13. In the figure, the locus of the point P' or the head of the players is displayed together with the images at the time of impact.

The display of a stick picture formed by connecting the motion points with lines is now described. As this embodiment uses TV images, the rate of 60 frames per sec. is set and the system processes images frame by frame. Therefore, it becomes possible to connect points of a swing in each frame and to display these linear components as a series of a continuous motion in the form of a stick pattern. The subject can easily evaluate his swing form by looking at the display where the contour of his movements is shown.

Figure 14:
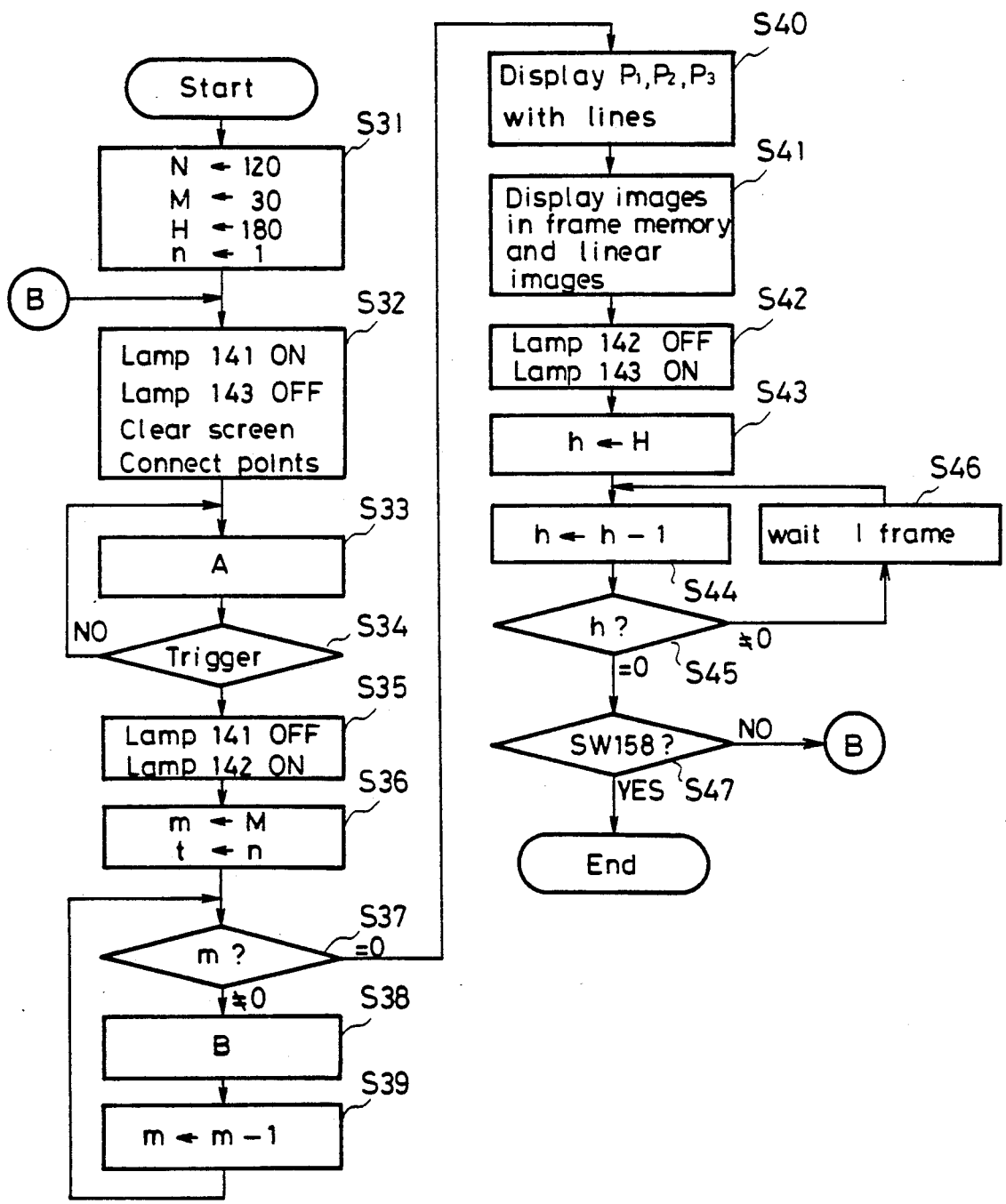
FIG. 14 is a flow chart showing the display operation of linear images.

FIG. 14 shows a flow chart of the linear display mentioned above. The linear display requires operations to compose the images and the linear images stored in the frame memory 220 and to display the two simultaneously. If linear image display alone is needed, the operation of storing and reproducing in and from the memory 220 may be omitted.

The system is initialized first (S31) to secure the memory capacity for 2 seconds or 120 frames in the memory 270 which is to store the measured values. The letter H denotes the duration of time for prohibiting updating of the frame memory after the trigger signal (impact time) and herein it is set at 180 frames (3 sec.) At the step S32, under the state of waiting for trigger (ready), the points $P_1$, $P_2$, and $P_3$ are connected by linear components and the screen is cleared. At the step S35 a trigger state is displayed, while at S42 the state of hold is shown by a lamp.

Figure 15:
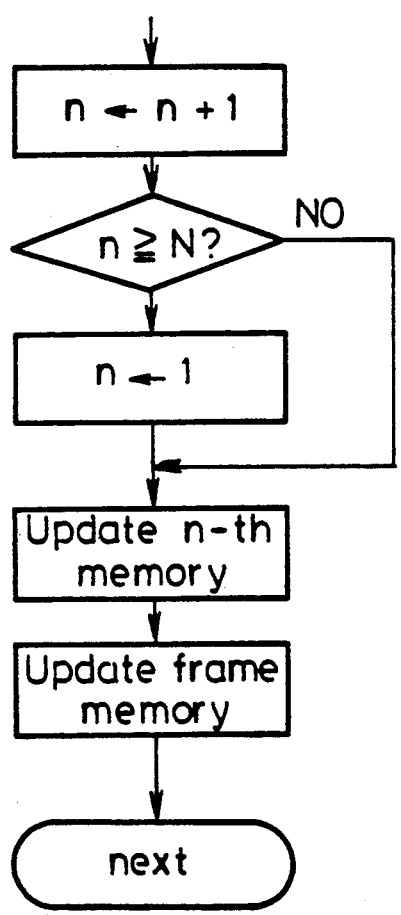
FIGS. 15 and 16 are flow charts showing the operation of FIG. 14.
Figure 16:
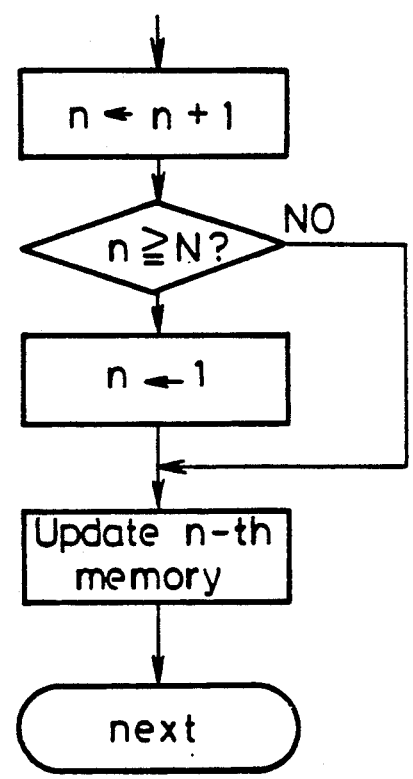

The processing shown in FIG. 15 is executed at the step S33. The n-th memory 270 is updated for holding the measured values while the frame memory 220 is being updated at the step S33. At the step S38, the n-th memory 270 of FIG. 16 is updated to wait for a swing at a trigger state.

When it is triggered at the step S34, the system is updated for the number of updated frames of the memory after the trigger by the steps S36 through 39. This achieves holding of the frame at the time of trigger. At the step S40, linear images obtained by connecting points $P_1$, $P_2$, and $P_3$ with lines are displayed. At the step S41, images at the impact time stored in the frame memory 220 are displayed in composition with the linear images in the unit 300.

At steps S43 through S46, the image signals stored in the frame memory 220 are controllably held for a predetermined duration of time once a trigger is issued.

By the above mentioned processing, the images stored in the frame memory 220 are composed with the linear images obtained by connecting the points $P_1$ through $P_3$ with lines and displayed.

Figure 17:
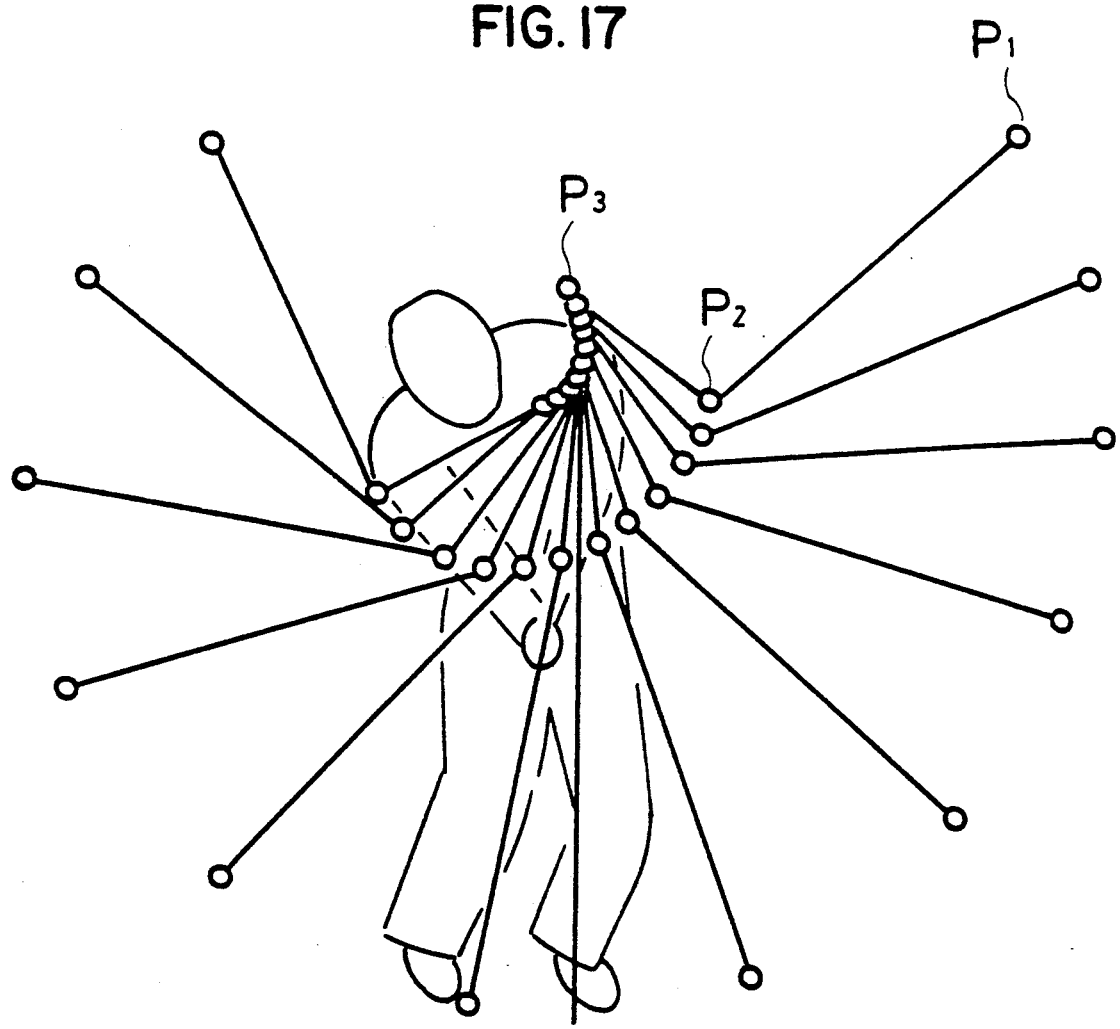
FIG. 17 is an example of linear displays.

Although the image signals stored in the frame memory 220 are outputted simultaneously in the above flow chart, if the operation for controlling the frame memory 220 is omitted, the stick pictures for the points $P_1$ through $P_3$ may be displayed. An example of a stick picture for the points $P_1$ through $P_3$ is shown in FIG. 17, but not all the linear components for all frames are shown. Only the selected lines are shown in order to simplify the description. By displaying motions in linear images, unnecessary movement of the body of a player entailed by his swing or his follow-through may be viewed in one screen.

In the operation of connecting the aforementioned points, it is possible to set point $P_2'$ to satisfy the equation, $1.1 \times P_3P_2 = P_3P_2'$ instead of connecting directly the points $P_1$, $P_2'$, and $P_3$, and to connect lines between $P_1$ and $P_2'$, and between $P_2'$ and $P_3$. This can correct deviation of the wrist of the player or the point $P_2$ as the point $P_2$ placed on his wrist does not necessarily coincide with the center of the curvature of the swing.

In the operation of connecting the points, it is preferable to obtain addresses of the points $P_1$ through $P_3$ at the time of impact, the location 45° before the impact, and the location 90° after the impact from the coordinates before and after and, to display them in stick pictures at above times in different colors.

The address may be calculated from the coordinates close thereto for the necessary angle or the time by calculation of interpolation or linear approximation which will be described hereinafter.

Figure 18:
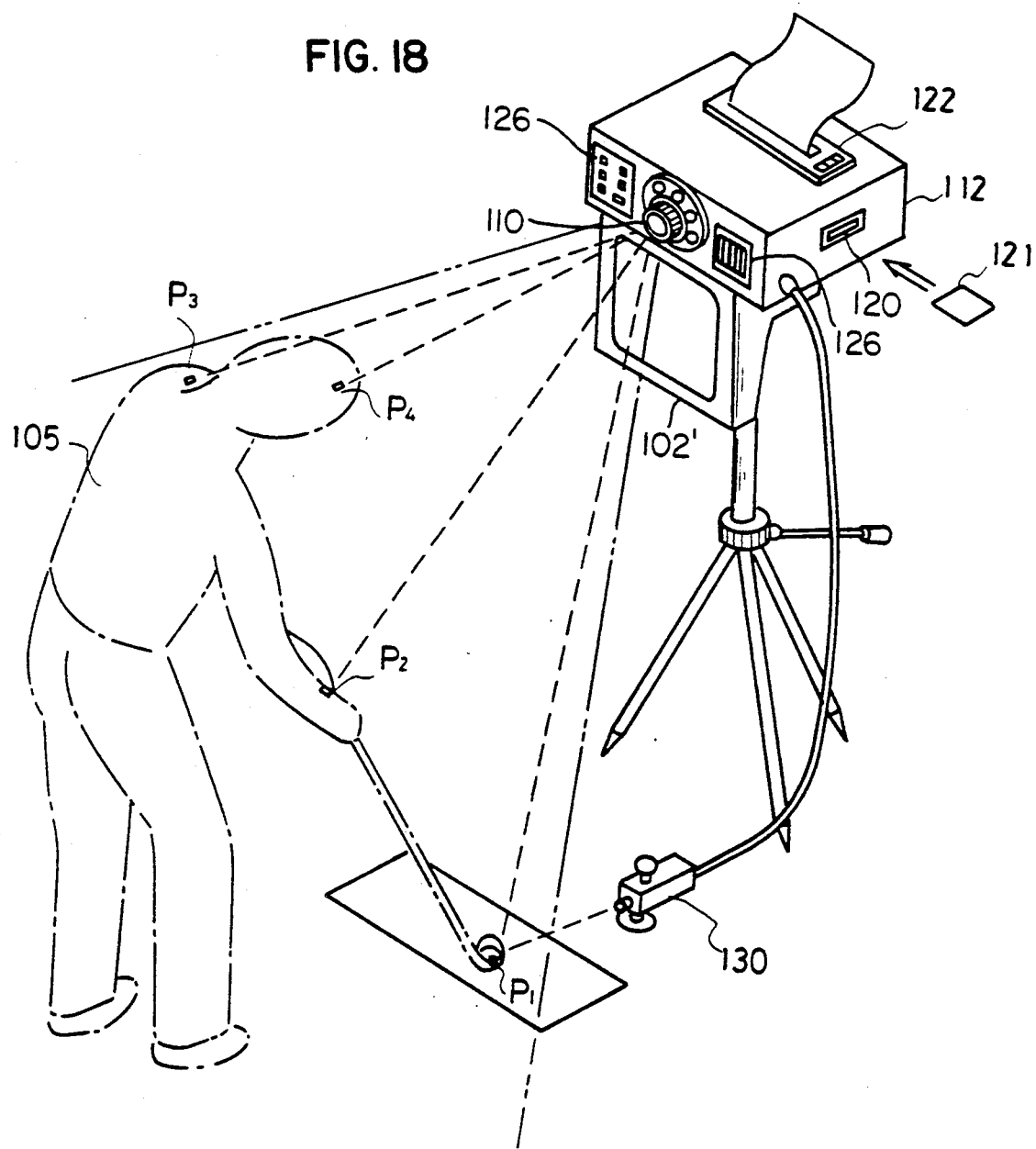
FIG. 18 shows another embodiment of this invention system.

FIG. 18 shows an embodiment of this invention's motion analyzing/advising system which is portable. The system is packaged in a portable case 112 and comprises an imaging unit 110, a display unit 102', an operation panel 104, a printer 122, a speaker 126, a microphone 128 (behind the speaker), and an IC card input-/output unit 120. Case 112 also includes a processor and an operation panel like items 103, 104 in FIG. 1. A plane display unit such as a liquid crystal display unit may be used as unit 102'. The system is provided with a battery power source for actuation. Unit 130 is a light sensor.

When in use, a subject player stands at a position facing the system, and swings. His motions are imaged by an imaging unit for measurement, and the measurement result is displayed on the display unit upon demand, outputted by a printer or stored in an IC card. In this embodiment, the trigger moment or the time of impact is detected by a sensor 130 provided at a position suitable for addressing, and a start switch is attached to the sensor.

Because triggering may be detected when the trigger conditions are satisfied, it is not always necessary to provide the sensor. As this system is actuated by a battery, it can conveniently be used at golf ranges or on the golf courses where no commercial power source is available.

Swings in images taken by VTR may be analyzed by this invention system. A VTR unit naturally may be used in place of a TV camera as the imaging unit 110.

Functions of speaker 126 and microphone 128 will now be described. The speaker 126 outputs voices or buzzing sound to indicate whether the trigger has been applied normally. This also functions to notify the end of a measurement. The microphone 128 may be used to indicate in voice the start of measurement instead of pressing the switch for start, but in this case provision of a voice sound processor is necessary.

The speaker may be used to output the result of the analysis of a swing (which will be described hereinafter) and a speech synthesizer is needed for this case.

Figure 19:
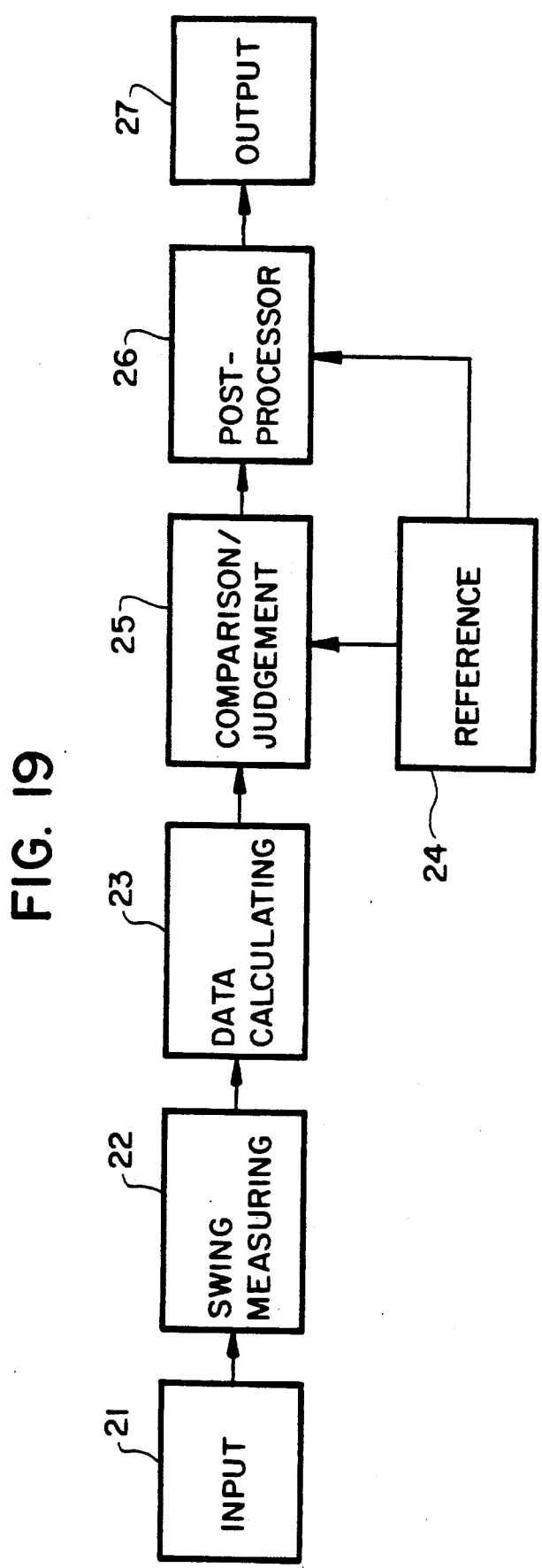
FIG. 19 shows the construction of a processing operation.

The explanation is now given to the operation related to the fourth aspect of this invention in which a swing of the subject player is compared with plural references and the result is outputted. FIG. 19 shows the structure of the processing steps. The unit includes an input means 21 which inputs data of a swing picked up by the imaging unit 110. Swing measuring means 22 extracts the data in the address of the point, which is a base for the analysis, by means of image processing technique. Data calculating means 23 extracts and calculates the speed, acceleration, angular speed or angular acceleration for each point out of the thus obtained positional data and obtains data groups matched with the reference. A comparison reference holding means 24 holds data for plural references and a comparison/judgement means 25 compares the calculated data with the reference data. Post-processor 26 selects diagnosis results for a particular reference out of the holding means 24 depending on the result of comparison and processes them for output in voice or image in the display, and an output means 27 outputs the result in image or voice.

Figure 20:
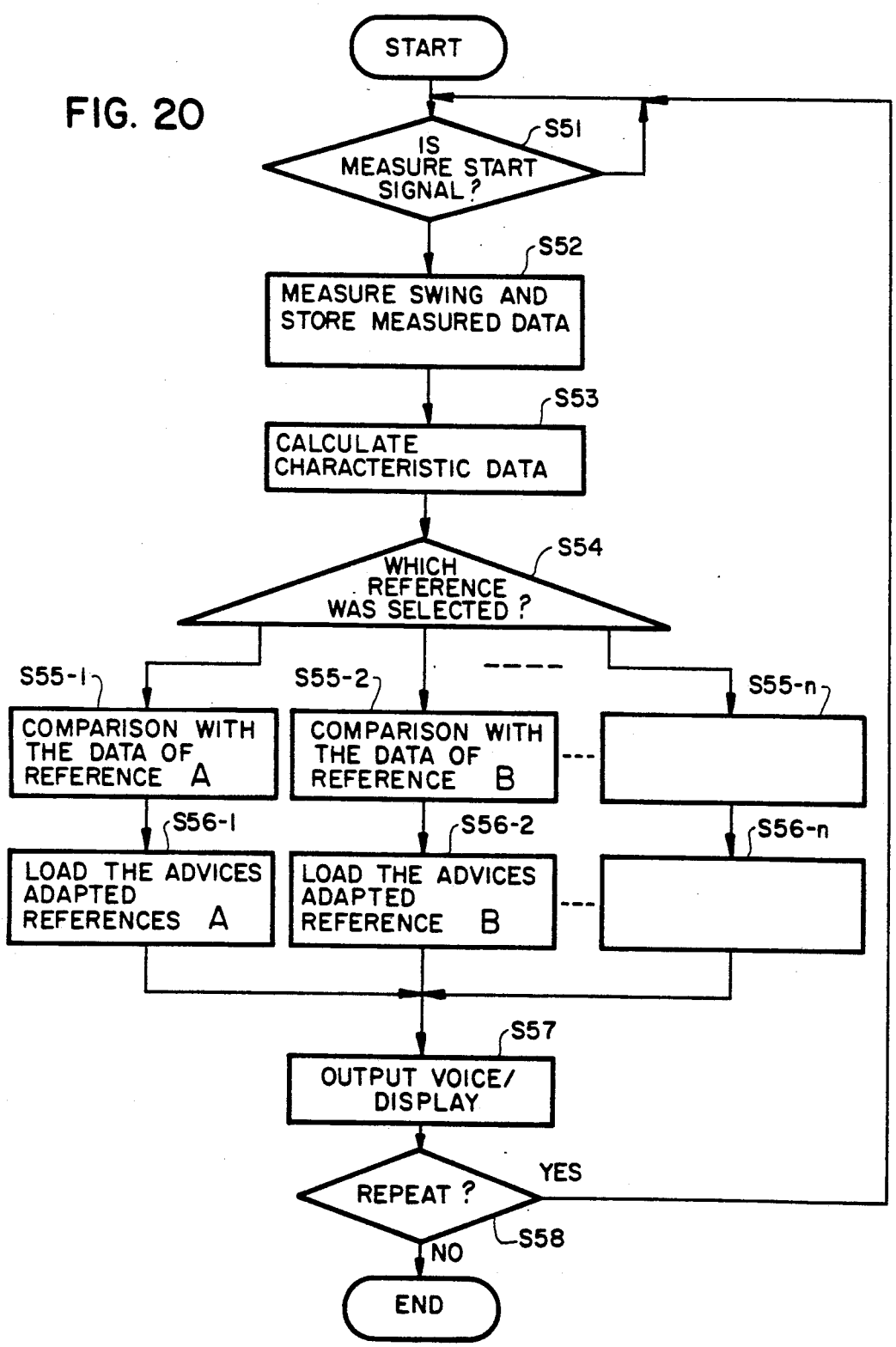
FIG. 20 is a flow chart showing the operation of an embodiment.

The operation of this embodiment system is now described referring to the flow chart shown in FIG. 20. A subject player selects a reference before actually starting the analysis by manipulating a switch 124 (FIG. 4). Alternatively, he may select a reference by inserting an IC card 121 or a similar memory card into an IC card input/output unit 120 which is provided as an exterior memory input/output unit for the unit 103. Data of the swings played by plural and different types of professional golf players are available as the references. For instance, a series of patterns comprising data groups are prepared to record analysis of the swings of such famous professional players as Tsune Nakajima, Masashi Ozaki, and Isao Aoki.

The measuring operation is started first; a swing of a subject player is picked up by the unit 110 including a TV camera 100 to measure the swing and to store the measured data (Step S52). The characteristic data is calculated out of the measured data (Step S53). The characterized data is compared with the selected reference data (Steps S55-1 through S55-$n$). The difference from the reference is obtained, and advices adapted to the references are loaded from the memory (Steps S56-1 through S56-$n$) and converted into voice for output (Step S57). If further analysis is required, processing is repeated. At the step S1 whether the measurement has been started is decided and at the step S58 whether it has ended is decided.

The operation of diagnosis processes is now described. The processing by CPU 260 is first described. CPU 260 processes the measurement and storage of a swing, and the calculation and comparison of the data performed at the steps S52 -S56.

Figure 21:
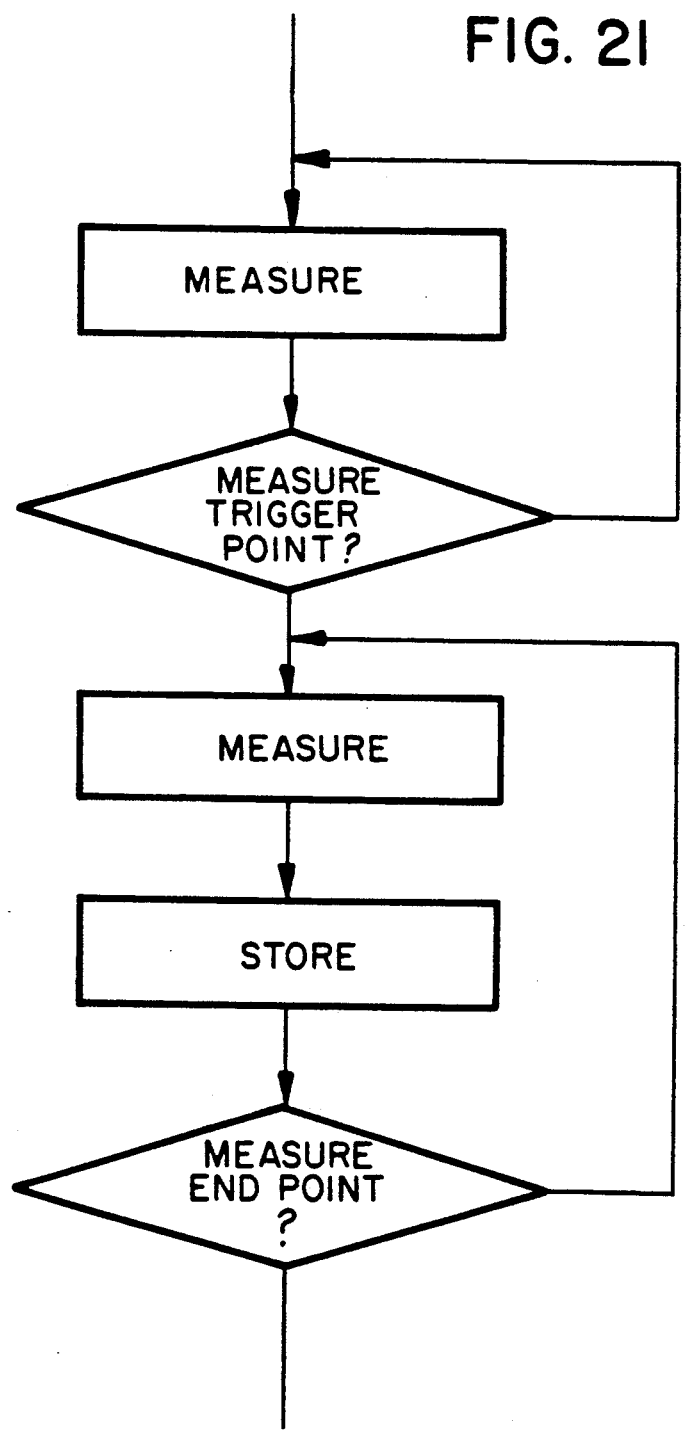
FIG. 21 is a flow chart showing the operation of an embodiment.

The measurement and storage of a swing is executed as below. FIG. 21 is a flow chart to show the details of the processing at the step S52. For measurement of a swing, the positional data for each point are calculated from the address signals of the points inputted from the circuit 250. More particularly, the centers of gravity are respectively calculated for the points $P_1$ through $P_6$. For the calculation X- and Y-coordinates inputted from the circuit 250 are added for each point. The number N of the signals inputted as the address of a point is counted and averaged in accordance with the formula, $X = \Sigma X/N$, $Y = \Sigma Y/N$. The obtained addresses are designated as the coordinates for the points and stored in the memory 270.

The positional addresses of each point and positional addresses defining a window with the point at the center thereof are outputted to the window signal generator 204 in order to align the window covering the measured data therein with the position of the point in a preceding image. The positional address to define a window may be predicted by comparing the preceding position of a point with the current position thereof and outputted to the circuit 204.

The measurement operation is conducted for all the images from the start point to the end point, and the extracted addresses indicating the movement at each point are stored in the memory 270.

The measurement of necessary data is started from the trigger point for measurement. The trigger point may be determined as the time when the club head reaches the highest position or the time when the angle of the club becomes 60° against the vertical direction or the time when the club passes over the head of a player from right to left. It may also be determined timewise such as the measurement should be triggered one second after the start button is pushed.

The end point is the time point when all the data necessary for analysis of a swing have been obtained, and may be any point during the follow-through after the impact. The end point is not necessarily set, and the operation may end when a predetermined duration of time has lapsed after the trigger point.

Then, the data are calculated to extract features of the swing of the player.

Figure 22:
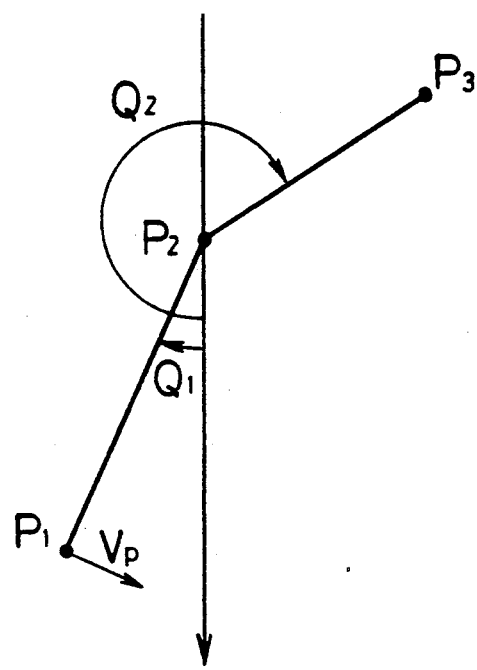
FIG. 22 is an explanatory view to show the relation between motion points and motion data.

The data are the speed of the club head $VP_1$, the angle of the club $\Theta_1$, the angle of the arm $\Theta_2$, the angular speed of the club $\Theta_1$, the angular speed of the arm $\Theta_2$, the angular speed ratio $\Theta_1/\Theta_2$, the angular acceleration of the club $\Theta_1$, the angular acceleration of the arm $\Theta_2$, and these data are calculated from the addresses of the points $P_1$ through $P_6$, and the obtained data are formulated in time series of sampled images in a table such as Table 1 below. The table shows only the data on the club head address $P_1$, the wrist address $P_2$ and the shoulder address $P_3$. FIG. 22 shows the relation between the points and data.

$T_2$: angle of the arm
$DT_1$: angular speed of the club
$DT_2$: angular speed of arm
PDT: angular speed ratio
$DDT_1$: angular acceleration of the club
$DDT_2$: angular acceleration of the arm.

Out of the data of the table, the data which coincide in measured time point with the peak time or the impact time and the reference model stored are calculated arithmetically.

Reading in of image data of the motion of the subject starts from the trigger point, but as the system does not sample and output the impact time when the subject hits the ball or the acceleration reaches its peak, it is necessary to obtain by arithmetic calculation the data at the peak for comparison purpose. The data preferably are taken at the time point coinciding with the reference data time point as the reference data should be those existing within a given time period or an angular interval from the impact time and at the peak value.

Timing of a swing may be judged good or bad by comparing the time or the address point of the peak

TABLE 1

| data | address $P_1$ of club head | | address $P_2$ of wrist | | address $P_3$ of shoulder | | | head speed | club angle | angle of arm | angular speed of club | angular speed of arm | angular speed ratio | angular speed of club | angular acceleration of arm |
|---|---|---|---|---|---|---|---|---|---|---|---|---|---|---|---|
| time t | X | Y | X | Y | X | Y | ... | $VP_1$ | $\theta_1$ | $\theta_2$ | $\theta_1$ | $\theta_2$ | $\theta_1/\theta_2$ | $\theta_1$ | $\theta_2$ |
| . | . | . | . | . | . | . | | . | . | . | . | . | . | . | . |
| . | . | . | . | . | . | . | | . | . | . | . | . | . | . | . |
| . | . | . | . | . | . | . | | . | . | . | . | . | . | . | . |
| $t_{n-1}$ | | | | | | | | $VP_{1n-1}$ | $T_{1n-1}$ | $T_{2n-1}$ | | | | | |
| $t_n$ | $x_{1n}$ | $y_{1n}$ | $x_{2n}$ | $y_{2n}$ | $x_{3n}$ | $y_{3n}$ | | $VP_{1n}$ | $T_{1n}$ | $T_{2n}$ | $DT_{1n}$ | $DT_{2n}$ | $PDT_n$ | $DDT_{1n}$ | $DDT_{2n}$ |
| $t_{n+1}$ | | | | | | | | $VP_{1n+1}$ | $T_{1n+1}$ | $T_{2n+1}$ | | | | | |
| . | . | . | . | . | . | . | | . | . | . | . | . | . | . | . |
| . | . | . | . | . | . | . | | . | . | . | . | . | . | . | . |
| . | . | . | . | . | . | . | | . | . | . | . | . | . | . | . |

The calculation to obtain such data is conducted using the positional addresses for points in accordance with the following equations.

$$VP_{1n} = \sqrt{(X_{1n} - X_{1n} - 1)^2 + (Y_{1n} - Y_{1n-1})}$$

$$T_{in} = \tan^{-1}[(X_{2n} - X_{in})/(Y_{2n} - Y_{in})]$$

$$T_{2n} = \tan^{-1}[(X_{3n} - X_{2n})/(Y_{3n} - Y_{2n})]$$

$$DT_{in} = T_{in} - T_{in-1}$$

$$DT_{2n} = T_{2n} - T_{2n-1}$$

$$PDT_n = DT_{in}/DT_{2n}$$

$$DDT_{in} = DT_{in} - DT_{in-1}$$

$$DDT_{2n} = DT_{2n} - DT_{2n-1}$$

wherein
VP: speed of the head
$T_1$: angle of the club speed of the head with those at the impact. It is also possible to judge whether or not the peak moves away from the center of revolution of the swing radially by comparing the peak of the angular acceleration of the arm with the peak of the angular acceleration of the club, a swing may be evaluated by obtaining timewise positions and peak values.

In order to obtain those data at the peak time or at the times necessary for such comparison, data should be interpolated from three points out of the aforementioned data. For instance, the peak time in angular speed may be calculated by the following equation if it is assumed that the club angular speed $D_{T1}$ represents the maximum value.

$$t_{peak} = t_n + 1/2 \frac{(DT_{1n-1} + DT_{1n+1})}{(DT_{1n-1} + DT_{1n+1} - 2 DT_{1n})} \Delta t$$

Similarly, the peak times may be obtained for the arm angular speed $DT_{2n}$, the club angular acceleration $DDT_{in}$, the arm angular acceleration $DDT_{2n}$. The peak value at the peak time may be obtained by interpolating the data before and after the time. The interpolation of the data may be performed by inserting the data of these three points by parabola approximation, circular approximation or linear calculation.

It is further possible to obtain the data at the three points by parabolic approximation by designating the address ($X_0$, $Y_0$) of the head which is designated before the start of measurement as the address of the impact time, and selecting three points having addresses approximate thereto. Instead of using the address, the coordinate position of the peak head speed is calculated by interpolation of the above mentioned peak value, and the time point is set as the impact time.

Figure 23:
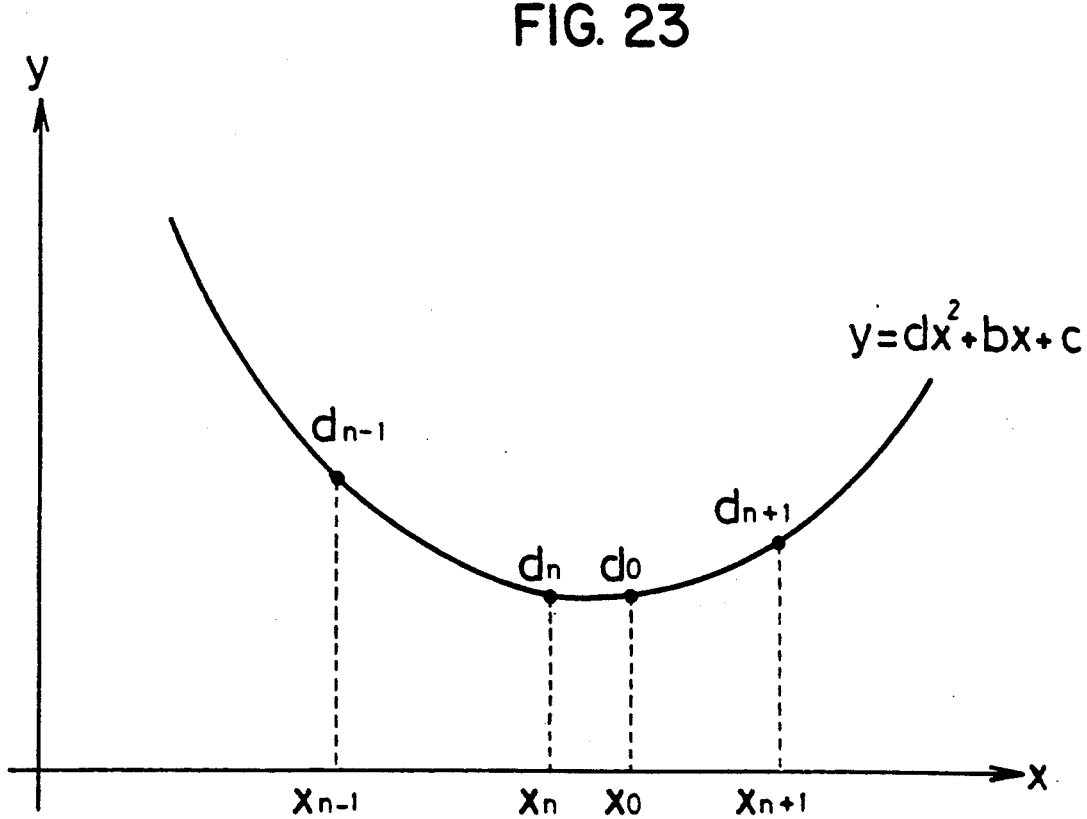
FIG. 23 is an explanatory view to show interpolation.

An example of interpolation with a parabola is described below with reference to FIG. 23; a parabola is expressed as $$y = ax^2 + bx + c \quad (1)$$

and the data at the 3 points $d_{n-1}$, $d_n$, and $d_{n+1}$ are represented as below;

$$d_{n-1} = ax_{n-1}^2 + bx_{n-1} + c \quad (2)$$

$$d_n = ax_n^2 + bx_n + c \quad (3)$$

$$d_{n+1} = ax_{n+1}^2 + bx_{n+1} + c \quad (4)$$

If the relation holds as $x_{n-1} < X_0 < X_{n+1}$, the data $d_0$ at the point x will be calculated by obtaining a, b, and c from the above simultaneous equations (2) through (4).

At the same time, the data as the reference data may be calculated similarly by interpolation or linear approximation. The obtained data will subsequently be compared with the reference data. As such reference data, the data on the characteristic motions of a swing by a professional golfer are prepared in advance in the form corresponding to the above Table 1.

When the data of the subject player has been extracted and calculated, the selected reference data are read out and the distance between the reference data and the subject data is measured. The distances should be obtained respectively at each comparison point for the speed of the head, arm angular speed, acceleration, angular acceleration, etc., and the differences of each data are calculated to obtain the square sum thereof. This allows one to judge how far the data of a swing by the subject is from the reference data.

The distance of the subject data from the reference data may differ depending on the reference selected and on the point prioritized, and therefore the data should be weighted. For instance, a subject who selected Masashi Ozaki, the professional golfer, may prioritize the distance in analysis. Therefore, the data relating to the distance should be weighted more. On the other hand, a subject who selected as his model Isao Aoki may prioritize the motion of his wrist, and more weight should be given to the movement of his wrist data.

In weighing in the comparison, parameters may be selected from the data collected from the swings of a particular golfer or of plural professional players using various statistic methods such as multivariate analysis.

When the distance between the subject data and the reference data or the evaluation is given, an advice according to the evaluation is outputted. Advices are prepared in advance corresponding to the respective references, and therefore an advice suitable to the selected reference will be given. This is because the check items differ depending on the model professional golfer. For instance, if the model is selected to be Masashi Ozaki, the items such as the swinging motion of the arms or twisting of the body will be checked, and advices with an emphasis on these items will be given.

An example of advice which will be outputted corresponding to the evaluation obtained by the comparison of a subject data with the model reference is now described.

In order to simplify the explanation, it is assumed that an advice is outputted based on the two kinds of data, i.e., angular velocity PDT at the time of impact and the head speed at the time $VP_1$ calculated by interpolation. It is assumed that the data obtained from analysis of the swing of the subject are PDT = 0.6, and $VP_1 = 45$ (m/s).

Table 2 shows as reference the angular speed $m_1$, and the head speed at the impact time $m_2$ of Isao Aoki and Masashi Ozaki, two professional golfers.

TABLE 2

| type | target value | |
|---|---|---|
| | angular speed ratio $m_1$ | head speed at impact time $m_2$ |
| Isao Aoki | 0.7 | 65 |
| Masashi Ozaki | 0.45 | 70 |

Table 3 shows weights $\omega$ of those two golfers.

TABLE 3

| type | weight | |
|---|---|---|
| | angular speed ratio $\omega_1$ | head speed at impact time $\omega_2$ |
| Isao Aoki | 0.8 | 0.2 |
| Masashi Ozaki | 0.3 | 0.7 |

By comparing the subject data with the reference data, a comprehensive evaluation point A is obtained by the following equation.

$$A = 100 \left( 1 - \sqrt{\omega_1 \left( \frac{PDT - m_1}{m_2} \right)^2 + \omega_2 \left( \frac{VP_1 - m_2}{m_2} \right)^2} \right)$$

If Isao Aoki is selected as the reference, the point is 81 while if Masashi Ozaki is selected, it is 61. An advice such that "Your total point is 81. It is almost close to the target swing. You had better turn the wrist back a bit quicker. The drive distance is long enough" will be given to the subject who selected Aoki. The subject who selected Ozaki is given an advice such that "Your total point is 61. You have a long way to reach the target. You had better swing your hip faster and with all your force".

The phrase following the total evaluation point is selected from Table 4 prepared in correspondence to evaluations.

TABLE 4

| total evaluation | phrase output |
|---|---|
| 100–90 | Your swing is as good as the target. |
| 90–70 | Your swing is almost as good as the target. |
| 70–50 | You have to take one more step to reach the target. |
| 50– | You have to go a long way to reach the target. |

The following phrases are prepared in advance in correspondence to the result of comparison in Table 5 and will be outputted depending on the difference between the subject data and the reference data.

TABLE 5

| comparison $VP_1-m_2$ | type | |
|---|---|---|
| | Masashi Ozaki advice | Isao Aoki advice |
| --5 | Distance is long enough. | Distance is long enough. |
| -5--15 | Distance is fairly long. | Distance is long enough. |
| -15--30 | You had better swing a bit more strongly. | Distance is fairly long |
| -30 | Your swing is not enough. | You had better swing with more force. |

The last phrase in the advice string relates to those on the wrist and the hip of the player, and are given in Table 6 depending on the comparison with the angular acceleration at the impact.

TABLE 6

| comparison $PDT-m_1$ | advice |
|---|---|
| 0.2 | You had better swing your hip a bit faster. |
| 0.5-0.2 | You had better swing your hip faster. |
| -0.5-0.5 | The wrist and hip motion are as good as the model. |
| -0.2--0.5 | You had better turn the wrist a little more quickly. |
| --0.2 | You had better turn the wrist quickly. |

Even if the data of two subjects are the same, different advices may be outputted depending on the target type.

The advice obtained by comparing with the reference are converted into voice signals by a converter, and outputted from the speaker 126 for the subject. Alternatively, they may be displayed in characters or images on the display unit 300.

Another embodiment will now be described. Unlike the first embodiment where a reference is selected as a target and a total evaluation is given depending on the difference of the subject's performance from the reference data and advice is outputted based on the evaluation, in this embodiment data of plural reference models which are various patterns of the golf swing are stored in memory, and the subject's data on his swings are compared with the plural reference data to judge to which reference the subject swing is closest.

This is determined by selecting a group of data suitable for judging classification of the swing such as the peak value or chronological interrelation thereof and comparing the group of data with the reference data selected similarly rather than comparing all the data. An evaluation is determined by extracting the difference between the subject data and the data of the closest reference pattern to output a suitable advice thereto.

In this embodiment, the plural references may include bad examples in addition to the model performance so that the swing of the subject is first judged to determine to which pattern it belongs, and then the type under which his swings fall is outputted with suitable advices.

Although in the aforementioned embodiment, the data comparison with the reference is made based on the data on the head speed, club angle, arm angle, club angular speed, angular velocity ratio, etc., the subject data may also be compared with other data. For example, evaluation may be given by comparison of the head speed at the peak value with that at impact, or the maximum club angular speed with the club angular speed at impact time. The time relation such as the peak value of the speeds of the impact, wrist or arm reaches the peak at what chronological relation with the impact time may be used for obtaining the evaluation. As a swing should be judged by the balance of the body motion when a subject swings, or efficiency of his movement, rather than the data merely on speed or acceleration, any reliable data to evaluate the swing may be used.

Although advices for the swing analyzed at the time are given in the above embodiments, the processor 103 may be provided with an output/input section connected to an outer memory, and the data and result of diagnoses are stored in the memory so that every time an analysis is made for a subject player, the data of the time may be compared with the previous data and evaluation. The result of the comparison will be outputted in phrases such as "Your swing of the arm is better than the last time, the turn of the wrist is also better than the last time".

The operation according to the fifth aspect of this invention is described below. The operation is described by referring to a case where memory timing for the frame memory is extracted out of the images of a golf swing of a desired state in the frame memory or the address data and images are held for reproduction. In storing images of the swing, when a subject 105 performs a swing, an angle Q in the frame memory 220 is designated in the direction vertical to the golf club so as to hold images of a downward swing at the time of impact. The angle Q is set by an operation panel 104, and more particularly by a switch 1166 thereon indicating trigger conditions.

Figure 24:
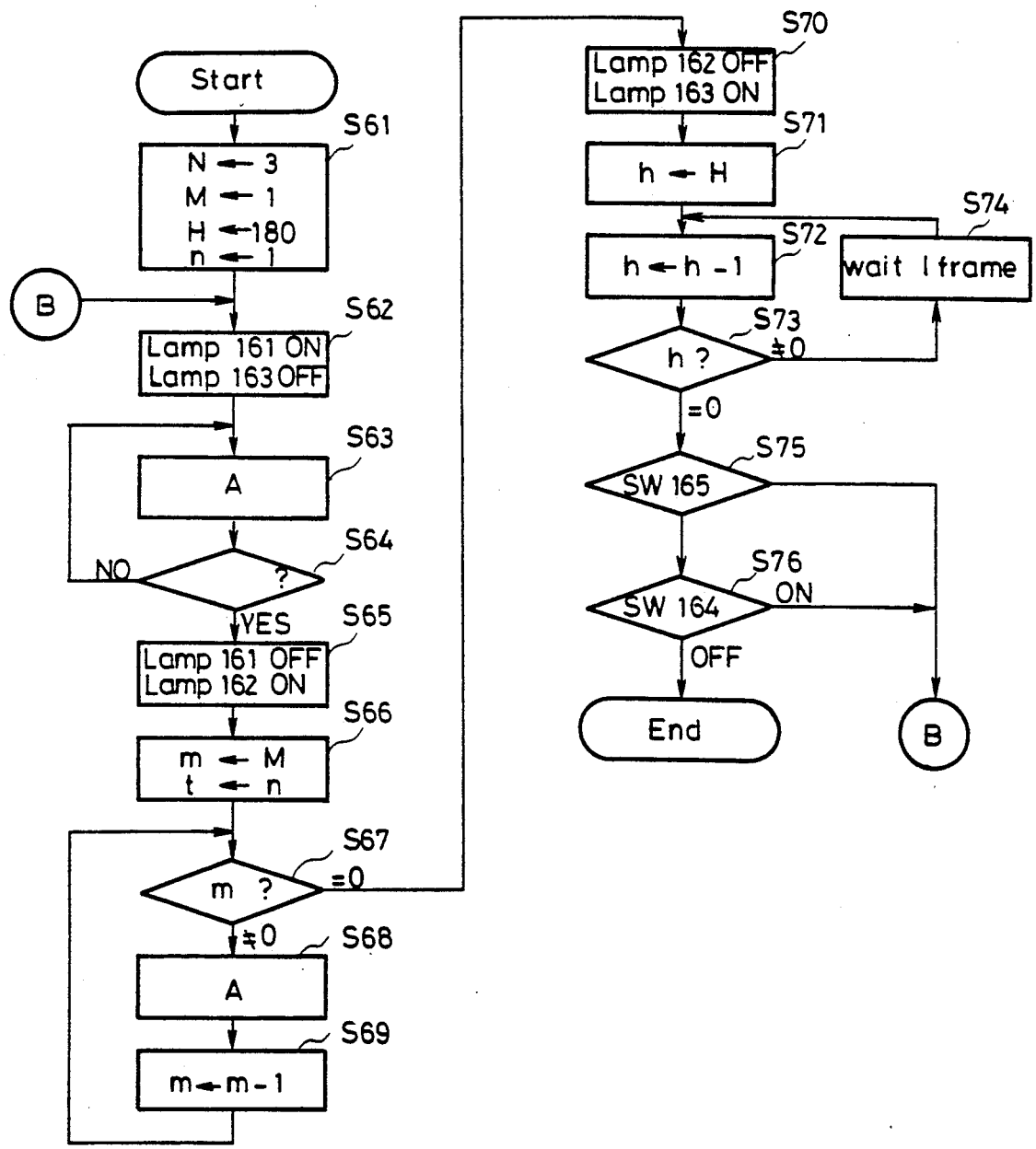
FIG. 24 is a flow chart showing the operation of an embodiment.

FIG. 24 is a flow chart to show the operation in measurement of a swing of a golf player. The system is first initialized (S61). More specifically, 3 is set for the number N in the frame memory 220. For H which is to be set for the duration of prohibiting trigger signal generation and in this case 180 frames or 3 sec. is set.

At the step S62, the state of waiting for trigger (ready) is displayed by a lamp, at the step S65 the state of trigger generation, and at the step S70, the state of holding.

At the step S63, the processing shown in FIG. 25 is conducted. More specifically, it is controlled to wait for a swing motion satisfying the trigger conditions while sequentially updating the frame memory 220. At the step S64 when the trigger conditions are met, the frame memory is updated for the amount after the trigger by the operations of the steps S66 through S69. When the angle of trigger is set at 0° by a switch 166, frames before and after the frame where the club angle Q turns from negative to positive will be held as the relation M=1 holds.

For the trigger, the following two conditions should be met at the same time.

Condition 11: $Q_L \times Q_{L-1} \leq 0$ and $Q_{L-1} \leq 0$
Condition 12: $X_L - X_{L-1}$ wherein $Q_L$ denotes the angle Q of the club at the time l, $X_L$ the X-coordinate at the time l of the motion point $P_1$, $Q_{L-1}$ the angle of the club of the time 1/60 sec. before the time l, $X_{L-1}$ the X-coordinate of the motion point $P_1$ at the time 1/60 sec. before the time l, and $\alpha$ the speed reference value at the point $P_1$. The reason why the condition of the speed of the club $\alpha$ is included in the trigger conditions is because it should be differentiated from the case where the subject swings the club lightly for trial. It may be the speed of 15 (m/s) or any speed so far as it can be differentiated from a trial swing.

When the angle Q of the club is set at 45° by the switch 166, the following three conditions should be satisfied at the same time for trigger.

Condition 21: $(Q_L-45)(Q_{L-1}-45) \leqq 0$ and $Q_{L-1}-45>0$

Condition 22: $X_L - X_{L-1} > \alpha'$

Condition 23: $Y_L - Y_{L-1} > \alpha''$ wherein $Y_L$ denotes Y-coordinate of the point $P_1$ at the time l, $Y_{L-1}$ the X-coordinate of the point $P_1$ at the time 1/60 Sec. before the time l, and $\alpha$ the speed reference value at the point $P_1$.

At the steps S71 through S74, once the trigger is set, image signals stored in the frame memory 220 are held for a prescribed duration of time.

When a continuous mode is designated by a switch 165, the procedure advances automatically to confirm the subsequent swing. But when the mode is for one-shot designated by the switch 1165, the content of the frame memory will be held until the time the switch 164 is pushed (S75, S76). The content of the three frame memories may be confirmed by reading another switch within the off-loop at the step S76 in an additional step or switching frame memories in the unit of a given time.

From the address positional data at the motion point $P_1$ of the club, whether the angle and speed conditions of the club and the club head are met is calculated, and if they are met, the image data before and after the time will be held in the frame memory 220. As there are forms stored before and after the trigger motion in the frame memory 220, if they are outputted on the display unit 300, swing forms at the time of impact can be diagnosed and analyzed.

FIG. 26 shows the structure of an image switch calculation circuit 2110. The operation thereof is now described. The circuit 210 may be switched between modes for single writing or superposition in the frame memory 220 to switch the input image signals therein. For superposition, two image signals inputted from the sampling circuit 200 and from the frame memory 220 are overlapped in output to the frame memory 220. More particularly, the circuit 210 comprises a comparator 3511 which compares the luminance of the image signals from the circuit 200 with the image signals from the frame memory 220. Buffer 352 buffers the image signals from the circuit 200, while buffer 353 buffers image signals from the frame memory 220. Switch 354 switches from the image signals from the sampling circuit 200 to the output image signals from the buffers 352 and 353 depending on the control from CPU 260.

The buffers 352, 353 output the input from comparator 351 only when selected, and provide a high impedance output when not selected. When the value of the image signals from the sampling circuit 200 is higher than that of the frame memory 220, the output from the buffer 352 is selected, while when it is smaller, the output from the buffer 353 is selected.

The switch 354 is selected depending on a singleshot mode or an overlapping mode of the frame memory 220. In the overlapping mode, the switch 354 conducts initialization of the frame memory 220 when the contact a on the side of the sampling circuit 200 is selected while it updates the frame memory 220 when the contact b is selected on the side of the buffers 352, 353. In the single-shot mode, the contact a is fixed.

The above operation is now described in more detail. In the mode of overlapping writing, unlike that of one-shot writing, the frame memory is not switched. For instance, a frame memory of n=1 is constantly used. For the number of times designated by M in the steps S67-S69, the frame memory 220 is overwritten with images of only the bright sections. As M=1, the images of the frame memory at the time of trigger are compared with the images of the frames inputted subsequently from the sampling circuit 200 so as to store photographic images which are multiple—exposed on the high luminance sections in the frame memory 220 and are taken out.

Figure 27:
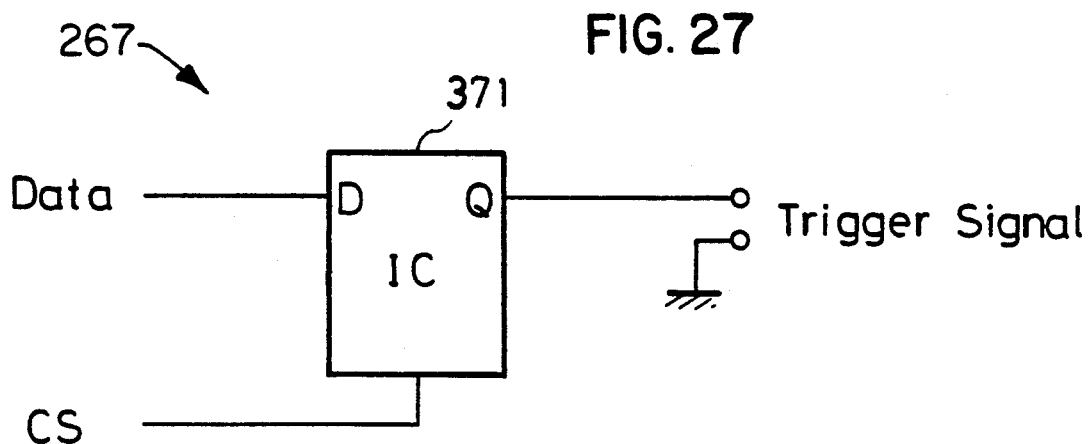
FIG. 27 shows a trigger signal output circuit.

FIG. 27 shows the structure of a trigger signal output circuit 267 (FIG. 4) wherein the output trigger signal is obtained by writing data from CPU 260 to IC 371 at the timing aligned with the ON/OFF operation of the trigger display lamp 162 on the panel 104. IC 371 is a D type flip-flop which latches on TTL. The above mentioned data may be inputted using a part of the data bus of CPU 260 while CS is obtained by decoding address signals. IC 371 may be SN74LS74A produced by T.I.

An embodiment wherein the trigger signals are used for control of the graphic memory 240 is now described below. For instance, from the point in time when all the trigger conditions are met, the operation of connecting the points $P_1$ and $P_2$ is repeated for M times, and the operation of connecting the points $P_{1L}$ and $P_{1L-1}$ is conducted for the point $P_1$, and the result is displayed.

This allows repeated display of the result of measurement of a golf swing after the impact in a stick picture or display of a downward swing at a specific point simply by setting the trigger conditions.

An embodiment where the trigger signals are used for control of the memory 270 will be described below. For instance, a memory 270 is assumed to be structured in a manner to hold 10 sets of the coordinates for the points $P_1$, $P_2$ and $P_3$, and the trigger conditions are set to satisfy the following three conditions simultaneously.

Condition 21: $(Q_{L-1}-45)(Q_{L-1}-45) \leqq 0$ and $Q_{L-1}-45>0$.

Condition 22: $X_L - X_{L-1} > \alpha'$

Condition 23: $Y_L - Y_{L-1} > \alpha''$

Then, four sets of the coordinates before those of the frame when the golf club crosses the point 45 degrees from the vertical direction thereof and five sets of coordinates thereafter and those of the frame will be held in the memory 270 by the trigger, and these 10 sets of the coordinates are used to analyze the swing of the player.

Description will be given to other cases. Although the above embodiment uses the trigger condition where the point P' comes to pass the position Q degrees from the vertical direction of the club, other trigger conditions may be set.

Figure 28:
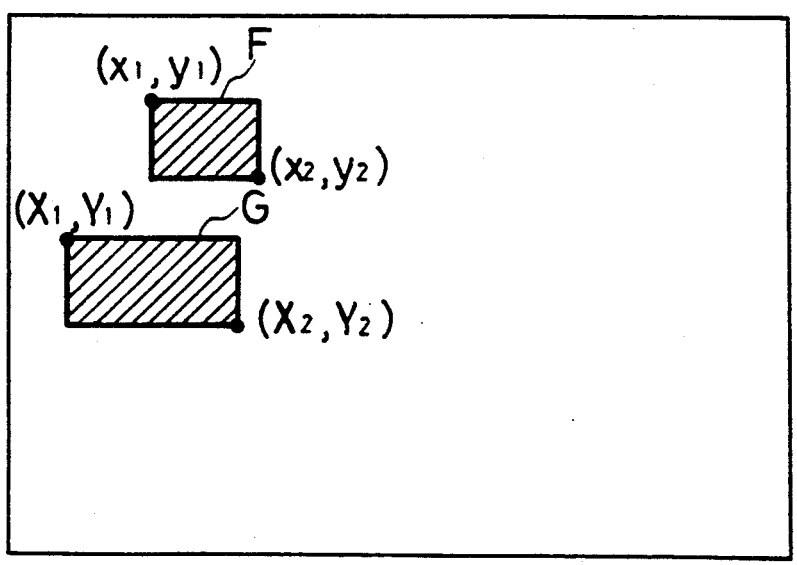
FIG. 28 shows an example of area designation.

For example, two areas may be set on the coordinates as shown in FIG. 28, and two conditions are set as below.

Condition 31: the point P, exists within the rectangular area F having vertices at points $(x_1, y_1)$ and $(x_2, y_2)$ Condition 32: the point $P_1$ exists within the rectangular area G having vertices at points $(X_1, Y_1)$ and $(X_2, Y_2)$ The trigger condition is set that within two frames the condition 32 exists after the condition 31 is not met any more.

By the above condition, the measurement may be triggered for a swing. More complicated operations may be performed if the trigger conditions are set using logical sum or multiplication or patterns of satisfaction/dissatisfaction.

The trigger conditions may be set by the number of times certain conditions are satisfied.

Modification to cover the cases where an analysis of a left-handed subject is desired or a mirror is used is now explained. When a mirror is provided between a subject 105 and a TV camera 100, trigger conditions may be set as follows. Use of a mirror can reduce the space required for installing this system quite advantageously, but the images outputted to the display 300 are opposite of those described above, and therefore the trigger conditions should be reversed. This may be attained by adding a switch for reversal at the interface 272 on the operation panel 104, giving address designations for reading out the horizontal line of pixels to the reading out circuits of the frame memory 220 and of the graphic memory 240 in the reversed order, and controlling the system to reverse the symbols of the X-coordinates at the operation points $P_1$, $P_2$ and $P_3$.

More specifically, the presence/absence of a mirror is set by a switch on the panel 104 and CPU 260 reads the information to reverse the address signal AX in the horizontal direction and the symbols of the X-coordinates for the points $P_1$ through $P_3$.

A similar operation is performed for a left-handed subject; the information is fed by operating a switch on the panel so that the information may be read in by CPU 160 which controls the system to reverse the symbols of the X-coordinates and the angles.

Although in the above embodiments a swing of a golf player is picked up by a camera and his swing at the impact time is stored in a frame memory, the same effect may be attained by using VTR.

The fifth aspect of the present invention is now described in respect of a modified embodiment. This modification is related to an inspection system for analyzing revolution of a tachometer.

Figure 29:
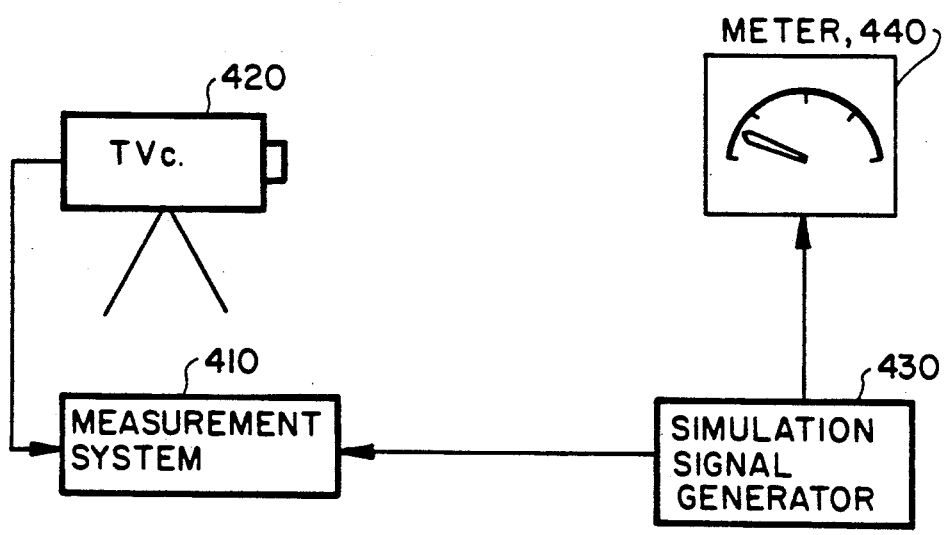
FIG. 29 is a chart showing the construction of a modified embodiment.

In this meter inspection system as shown in FIG. 29, ignition signals simulated from a simulation signal generator 430 are used to drive a meter 440, and the movement thereof is imaged by a TV camera 420 so as to inspect the meter 440.

Figure 30:
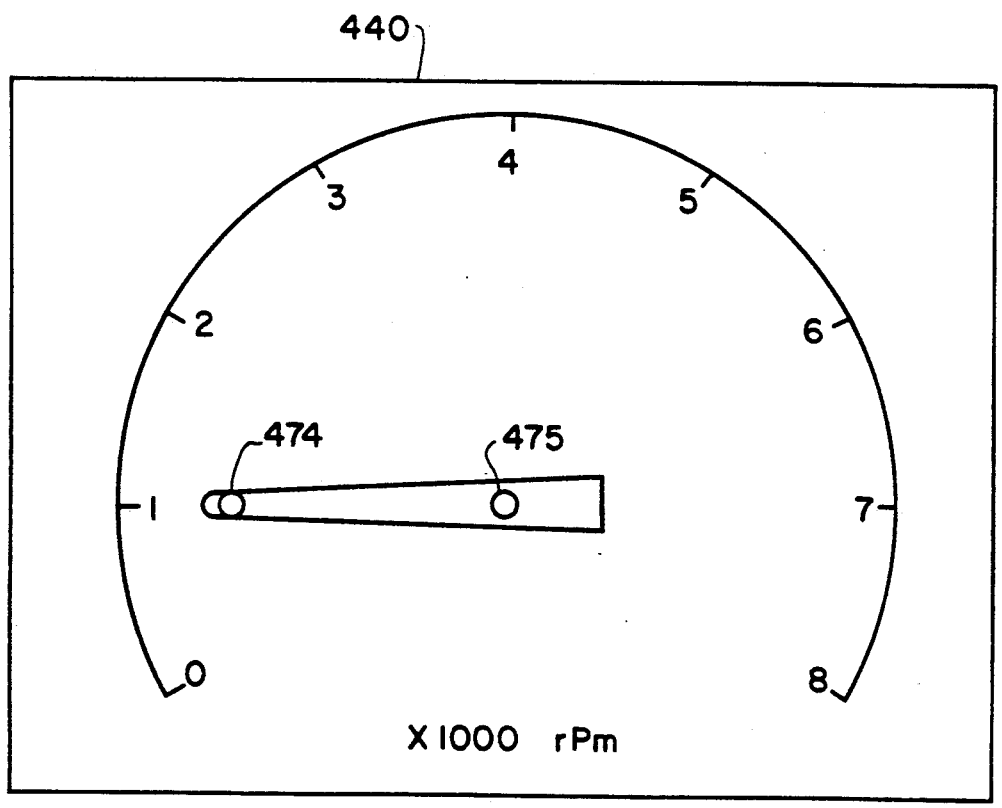
FIG. 30 shows an embodiment of an indicator.

The operation of the system is described below. As shown in FIG. 30, a pointer of the meter 440 or the subject of the inspection is provided with markers 474 and 475 respectively at the tip end and the center of rotation, and the address positional data of the markers 474, 475 are calculated by a coordinate calculator. When the rotational angle 8 of the pointer becomes constant and reaches a prescribed angle, or in other words the marker 474 marks a prescribed angle from the marker 475, for instance 90 degrees from the vertical direction, the system is triggered, and the movement of the pointer is measured for analysis of features.

In the prior art, a trigger signal generator is additionally provided to give trigger signals for starting the measurement to the measurement system 410 and the simulation signal generator 430 so that the generator 430 starts output of simulated signals with the trigger signals to take in the movement of the meter by the unit 410. In this embodiment, the speed or the smoothness of the pointer in the meter may be automatically measured.

Figure 31:
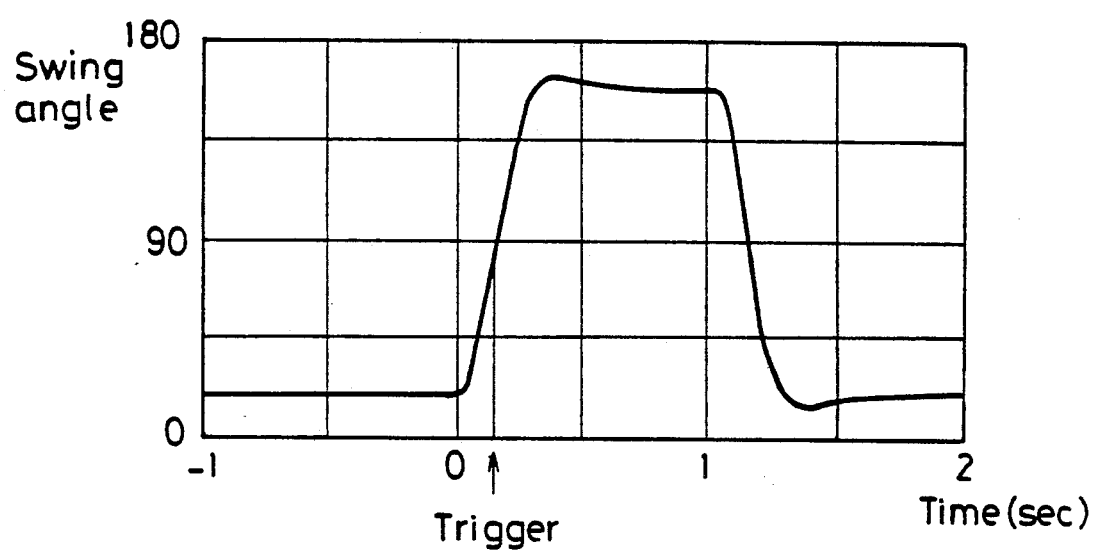
FIG. 31 shows an example of measurement.

FIG. 31 shows an example wherein the meter 440 is moved stepwise between 0 rpm and 3000 rpm and the dynamic characteristics thereof are measured. The measurement is triggered when the following condition 41 is met wherein t is the time and Q the angle.

Condition 41: $(Q_L - 90)(Q_{L-1} - 90) \leq 0$ and $Q_{L-1} - 90 > 0$.

This means the unit is triggered at the time point when the pointer passes the gauge of 1000 rpm or forms the angle of 90° from the vertical direction, and data before and after the desired time point will be taken in for measurement. This enables the circuit 430 to control the simulation of the signals irrespective of the measurement unit, making design of the total system easier. This also enables analysis of the relation between the control signal simulated by the circuit and the actual movement of the meter by taking in the data with the trigger signals.

The structure mentioned above may be applicable to the system for inspecting for acceptance the products which are transported on a conveyor belt by setting various trigger conditions depending on the features of the products. This system is also applicable to the behavioral analysis of animals.

Although the trigger conditions are set for starting measurement in the above embodiment and the modification according to the fifth aspect of this invention, it may be set for ending or suspending. For instance, an operation which cannot possibly occur during the measurement is set as a trigger condition, and if this condition is detected, the system is controlled to suspend the measurement operation and to return the procedure to the initial ready state or the state to receive trigger signals. If a condition to end the measurement is set, the measurement operation can be controlled for completion when this condition is detected.

Trigger conditions may be set in a plural number: i.e. conditions to start, suspend and end are set in advance and when any of them is detected, it is controlled accordingly. The effect of the measurement operation is therefore enhanced.

The foregoing description should not be considered limitative since this invention includes equivalents and is defined by the following claims.

What is claimed is:

1. A motion analyzing/advising system comprising:
   means to sample images of picked up motion of a subject and convert said images into digital signal indicative thereof,
   measurement means to measure respective coordinates of plural motion points of said picked up motions, each of said plural motion points preset for analyzing said motions of the subject,
   calculating means to extract coordinate data of said plural motion points from the converted digital signals,
   trigger detector means to detect whether said motion points satisfy preset trigger conditions for starting, suspending or ending a measurement operation based on said coordinate data and to automatically provided an appropriate trigger signal when said preset trigger conditions are satisfied.
   means to start, suspend or end the measurement operation based on said trigger signal provided by said trigger detector means, data calculating means to extract typical motion behavior from the coordinate of each motion point obtained by said measurement means, evaluation means to compare said typical motion behavior with a reference motion, and advising means to select and output an advising comment in accordance with the evaluation, said advising comment based on an amount of difference between said typical motion behavior and said reference motion.

2. The motion analyzing/advising system as claimed in claim 1 further comprising means for storing plural evaluation references, and means to select one reference among said plural evaluation references and the means to compare compares the selected reference with each motion behavior.

3. The motion analyzing/advising system as claimed in claim 1 wherein said trigger detector means further comprises means to detect an angle of connected lines of motion points as said preset trigger condition.

4. The motion analyzing/advising system as claimed in claim 1 wherein said trigger detector means further comprises means to detect an angular velocity of connected lines of motion points as said preset trigger condition.

5. The motion analyzing/advising system as claimed in claim 1 further comprising image memory means to store said images, and means for displaying tracks of at least one motion point simultaneously with the images stored in said image memory means at a prescribed triggering time.

6. A motion analyzing/advising system comprising:
means to sample images of picked up motions of a subject and to digitize said motions into digital signals,
calculating means to extract coordinate data of said plural motion points from the converted digital signals,
trigger detector means to detect whether said motion points satisfy preset trigger conditions for starting, suspending or ending a measurement operation based on said coordinate data and to automatically provide an appropriate trigger signal when said preset trigger conditions are satisfied,
means to start, suspend or end the measurement operation based on a trigger signal provided by said trigger detector means,
display means to display the result of the measurement by said measurement means, said display means including:
a) means to display connected lines of the motion points on said display means and
b) means to display the lines for a plural number of frames on said display means.

7. The motion analyzing/advising system as claimed in claim 6 further comprising means to obtain coordinate data of motion points at preset points by interpolation, and means to display the connected lines obtained by said interpolation at a designated time after said trigger signal indicative of the end of said measurement operation, said connected lines being displayed on said display means with emphasis thereon.

8. The motion analyzing/advising system as claimed in claim 6 or 7 including an image memory means to store picked up images and means to superimpose the connected lines on the images stored in said image memory means.

9. A motion analyzing/advising system comprising:

means to sample images of picked up motions of a subject and convert said images into digital signals indicative thereof, measurement means to measure respective coordinates of plural motion points of said picked up motions, each of said plural motion points preset for analyzing said motions of the subject.

data calculating means to extract typical motion behavior from the coordinate of each motion point obtained by said measurement means, evaluation means to compare said typical motion behavior with a reference motion, and advising means to select and output an advising comment in accordance with an evaluation done by the evaluation means, said advising comment based on an amount of difference between said typical motion behavior and said reference motion.

10. The motion analyzing/advising system as claimed in claim 9 further comprising means for storing plural evaluation references, and a means to diagnose which evaluation reference applies to each motion behavior.

11. The motion analyzing/advising system as claimed in claim 10 including means to select one reference among said evaluation references and the means to compare compares the selected reference with each motion behavior.

12. The motion analyzing/advising system as claimed in any one of the claims 9 through 11 wherein the data calculating means includes to interpolate each motion behavior at identical points to those of the reference data.

13. The motion analyzing/advising system as claimed in any one of the claims 9 through 11 wherein the measurement means includes means to track one or more motion point(s) over a designated displaying area and outputs the coordinates data of the motion point(s).

14. The motion analyzing/advising system as claimed in any one of the claims 9 through 11 wherein said advising means includes means for announcing the result of the evaluation in voice.

15. A system as in claim 9 wherein said advising means includes a plurality of preset advises stored therein, and means for selecting one of said advises based on said amount of difference between said typical motion behavior and said reference motion.

16. A motion analyzing/advising system which monitors images of motions of a subject, comprising:
means to sample and convert the images of the motions of a subject into digital signals indicative thereof,
calculating means to extract coordinate data of one or more motion points from the converted digital signals,
trigger detector means to detect whether said motion points satisfy preset trigger conditions for starting, suspending or ending a measurement operation based on said coordinate data and to automatically provide an appropriate trigger signal when said preset trigger conditions are satisfied, and
means to start, suspend or end the measurement operation based on said trigger signal provided by said trigger detector means.

17. The motion analyzing/advising system as claimed in claim 16 wherein said trigger detector means further comprises means to detect an angle of a connected line of motion points, said angle being one of said trigger conditions.

18. The motion analyzing/advising system as claimed in claim 16 wherein said trigger detector means further comprises means to detect an angular velocity of connected lines of motion points as said preset trigger condition.

19. The motion analyzing/advising system as claimed in claim 16 wherein said trigger detector means further comprises means to detect passing speed of the motion points over the designated area as said preset trigger condition.

20. The motion analyzing/advising system as claimed in any one of the claims 16 through 19 including means to store one or more frames of picked up images in frame memories with the trigger signals.

21. The motion analyzing/advising system as claimed in claim 20 including means to superimpose the stored image to a newly picked up image and to store the superimposed image in the frame memories.

22. The motion analyzing/advising system as claimed by any one of the claims 16 through 19 including means to reverse images and means to reverse coordinate data of motion points.

23. The motion measurement system as claimed in any one of the claims 16 through 19 including at least one memory means to store the results of measurement, and means to execute writing of a measurement result into said memory means with the trigger signals.

* * * * *